United States Patent [19]
Wythes et al.

[11] Patent Number: 5,639,779
[45] Date of Patent: Jun. 17, 1997

[54] INDOLE DERIVATIVES AS 5-HT1-LIKE AGONISTS

[75] Inventors: Martin James Wythes, Sandwich, United Kingdom; John Eugene Macor, Groton, Conn.

[73] Assignee: Pfizer Inc., New York, N.Y.

[21] Appl. No.: 313,106

[22] PCT Filed: Mar. 25, 1993

[86] PCT No.: PCT/EP93/00738

§ 371 Date: Oct. 6, 1994

§ 102(e) Date: Oct. 6, 1994

[87] PCT Pub. No.: WO93/21177

PCT Pub. Date: Oct. 28, 1993

[30] Foreign Application Priority Data

Apr. 10, 1992 [GB] United Kingdom ............... 9207930

[51] Int. Cl.⁶ .................. C07D 401/14; C07D 403/06; A61K 31/40
[52] U.S. Cl. .................. 514/414; 514/339; 546/277.4; 548/468
[58] Field of Search ............... 548/468; 514/414, 514/339; 546/277.4

[56] References Cited

U.S. PATENT DOCUMENTS

| | | | |
|---|---|---|---|
| 4,252,803 | 2/1981 | Webb | 424/248.5 |
| 4,839,377 | 6/1989 | Bays et al. | 514/415 |
| 4,855,314 | 8/1989 | Oxford et al. | 514/415 |
| 5,208,248 | 5/1993 | Baker et al. | 514/364 |
| 5,409,941 | 4/1995 | Nowakowski | 514/339 |

FOREIGN PATENT DOCUMENTS

| | | |
|---|---|---|
| 0303506 | 8/1988 | European Pat. Off. |
| 0313397 | 10/1988 | European Pat. Off. |
| 0354777 | 8/1989 | European Pat. Off. |
| 0438230 | 7/1991 | European Pat. Off. |
| 0497512 | 8/1992 | European Pat. Off. |
| 2083463 | 8/1981 | United Kingdom |
| 9118897 | 12/1991 | WIPO |
| 9206973 | 4/1992 | WIPO |

OTHER PUBLICATIONS

W. Feniuk, et al., P.P.A. Humphrey & M. J. Perren —Br. J. Pharmacol. (1989), 96, 83–90.

P.P.A. Humphrey, et al. —Br. J. Pharmacol. (1988), 94, 1123–1132.

R. E. Heuring et al. *J. Neuroscience*, 7, 894 (1987).

*Primary Examiner*—Jacqueline Haley
*Attorney, Agent, or Firm*—Peter C. Richardson; Paul H. Ginsburg; Grover F. Fuller, Jr.

[57] ABSTRACT

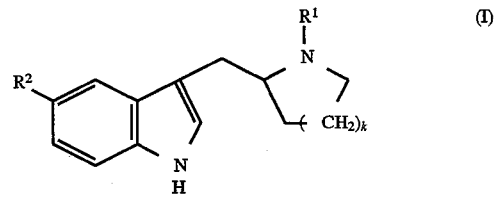

Compounds of formula (I) and pharmaceutically acceptable salts thereof, wherein $R^1$ is a substituted alkylene; $C_3$–$C_7$ cycloalkyl optionally substituted with HO; $C_3$–$C_6$ alkenyl optionally substituted with aryl; $C_5$–$C_7$ cycloalkenyl; or $C_3$–$C_6$ alkynyl; $R^2$ is H; halo; $F_3C$; NC; $R^8R^9NOC$; a substituted alkylene; $R^8R^9NO_2S$; $R^{10}S(O)_m$; $R^{12}CON(R^{11})$; $R^{10}SO_2N(R^{11})$; $R^8R^9NOCN(R^{11})$; $R^{10}O_2CN(R^{11})$; $R^{13}(CH_2)_nCH=CH$; or $R^7O$ are selective 5-HT$_1$-like receptor agonists useful in the treatment of migraine, cluster headache, chronic paroxysmal hemicrania and headache associated with vascular disorders.

8 Claims, No Drawings

INDOLE DERIVATIVES AS 5-HT1-LIKE AGONISTS

This application is a National Stage application of PCT/EP93/00738 filed Mar. 25, 1993 and published as WO 93/21177 on Oct. 28, 1993.

The present invention relates to indole derivatives which act on 5-hydroxytryptamine (5-HT) receptors.

More particularly the present invention relates to 3,5-disubstituted indoles which are selective agonists at the "5-HT$_1$-like" subtype of the 5-hydroxytryptamine receptor. Such "5-HT$_1$-like" receptors are present in the carotid vascular bed and their activation causes vasoconstriction with a consequent reduction in carotid blood flow. Compounds which have "5-HT$_1$-like" agonist activity are therefore useful in the treatment of medical conditions which are thought to result from excessive dilation of the carotid bed, such as migraine, cluster headache, chronic paroxysmal hemicrania and headache associated with vascular disorders. Certain compounds of the present invention are also agonists at central 5-HT$_1$ receptors and are therefore useful for the treatment of depression, anxiety, eating disorders, obesity and drug abuse.

The present invention provides compounds of formula:

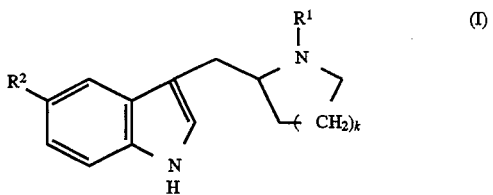

and pharmaceutically acceptable salts thereof, wherein $R^1$ is $(R^3CO)$ $C_1$–$C_3$ alkylene; $(R^4O_2C)$ $C_1$–$C_3$ alkylene; $(R^5R^6NOC)$ $C_1$–$C_3$ alkylene; $(R^5R^6NO_2S)C_1$–$C_3$ alkylene; $[R^3S(O)_m]C_1$–$C_3$ alkylene; $(R^7O)$ $C_2$–$C_4$ alkylene; $(C_3$–$C_7$ cycloalkyl) $C_1$–$C_3$ alkylene; (aryl) $C_1$–$C_3$ alkylene; (heteroaryl)$C_1$–$C_3$ alkylene; $C_3$–$C_7$ cycloalkyl optionally substituted with HO; $C_3$–$C_6$ alkenyl optionally substituted with aryl; $C_5$–$C_7$ cycloalkenyl; or $C_3$–$C_6$ alkynyl;

$R^2$ is H; halo; $F_3C$; NC; $R^8R^9NOC$; $(R^8R^9NOC)C_1$–$C_3$ alkylene; $R^8R^9NO_2S$; $(R^8R^9NO_2S)$ $C_1$–$C_3$ alkylene; $R^{10}S$ $(O)_m$; $[R^{10}S$ $(O)_m]C_1$–$C_3$ alkylene; $R^{12}CON$ $(R^{11})$; $[R^{12}CON(R^{11})]C_1$–$C_3$ alkylene; $R^{10}SO_2N(R^{11})$; $[R^{10}SO_2N(R^{11})]C_1$–$C_3$ alkylene; $R^8R^9NOCN(R^{11})$; $[R^8R^9NOCN(R^{11})]C_1$–$C_3$ alkylene; $R^{10}O_2CN(R^{11})$; $[R^{10}O_2CN(R^{11})]C_1$–$C_3$ alkylene; $R^{13}(CH_2)_nCH=CH$; or $R^7O$;

$R^3$ is $C_1$–$C_6$ alkyl; $(C_3$–$C_7$ cycloalkyl)$C_1$–$C_3$ alkylene; (aryl) $C_1$–$C_3$ alkylene; $C_3$–$C_7$ cycloalkyl; or aryl;

$R^4$ is $C_1$–$C_6$ alkyl; $(C_3$–$C_7$ cycloalkyl)$C_1$–$C_3$ alkylene; (aryl)$C_1$–$C_3$ alkylene; or $C_3$–$C_7$ cycloalkyl;

$R^5$ and $R^6$ are each independently selected from H; $C_1$–$C_6$ alkyl; $(C_3$–$C_7$ cycloalkyl)$C_1$–$C_3$ alkylene; (aryl)$C_1$–$C_3$ alkylene; and $C_3$–$C_7$ cycloalkyl;

or $R^5$ and $R^6$ together with the nitrogen atom to which they are attached form a 4- to 7-membered heterocyclic ring which may optionally incorporate a further heteroatom linkage selected from O, $S(O)_m$, NH, $N(C_1$–$C_4$ alkyl), and $N(C_1$–$C_5$ alkanoyl);

$R^7$ is H; $C_1$–$C_6$ alkyl; $(C_3$–$C_7$ cycloalkyl)$C_1$–$C_3$ alkylene; (aryl)$C_1$–$C_3$ alkylene; $C_3$–$C_7$ cycloalkyl; or aryl;

$R^8$ and $R^9$ are each independently selected from H; $C_1$–$C_6$ alkyl; $(C_3$–$C_7$ cycloalkyl)$C_1$–$C_3$ alkylene; (aryl)$C_1$–$C_3$ alkylene; and $C_3$–$C_7$ cycloalkyl;

or $R^8$ and $R^9$ together with the nitrogen atom to which they are attached form a 4- to 7-membered heterocyclic ring which may optionally incorporate a further heteroatom linkage selected from O, $S(O)_m$, NH, $N(C_1$–$C_4$ alkyl), and $N(C_1$–$C_5$ alkanoyl);

$R^{10}$ is $C_1$–$C_6$ alkyl; $(C_3$–$C_7$ cycloalkyl)$C_1$–$C_3$ alkylene; (aryl)$C_1$–$C_3$ alkylene; $C_3C_7$ cycloalkyl; or aryl;

$R^{11}$ and $R^{12}$ are each independently selected from H; $C_1$–$C_6$ alkyl; $(C_3$–$C_7$ cycloalkyl)$C_1$–$C_3$ alkylene; (aryl) $C_1$–$C_3$ alkylene; $C_3$–$C_7$ cycloalkyl; and aryl;

$R^{13}$ is selected from $R^8R^9NOC$; $R^8R^9NO_2S$; $R^{10}S(O)_m$; $R^{12}CON(R^{11})$; $R^{10}SO_2N(R^{11})$; $R^8R^9NOCN(R_{11})$; and $R^{10}O_2CN(R^{11})$; wherein $R^8$, $R^9$, $R^{10}$, $R^{11}$ and $R^{12}$ are as defined above; and k, m and n are each independently selected from 0, 1 and 2.

In the above definition, aryl means phenyl optionally substituted with one to three substituents independently selected from $C_1$–$C_4$ alkyl, $C_1$–$C_4$ alkoxy, halo, $F_3C$, NC, $H_2NOC$, and HO; heteroaryl means pyrrolyl, furyl, thienyl, oxazolyl, thialolyl, pyridyl, pyrimidinyl or pyrazinyl; and halo means fluoro, chloro, bromo or iodo.

Unless otherwise indicated, alkylene groups having two or more carbon atoms, alkyl and alkoxy groups having three or more carbon atoms, and alkanoyl, alkenyl and alkynyl groups having four or more carbon atoms, may be straight chain or branched chain.

The compounds of formula (I) may contain one or more asymmetric centres and thus can exist as stereoisomers, i.e. as enantiomers or as diastereoisomers. Furthermore, compounds of formula (I) which contain alkenyl groups can exist as cis-stereoisomers or trans-stereoisomers. In each instance, the invention includes both the separated individual stereoisomers as well as mixtures thereof.

The preferred stereoisomers are those which possess the R-configuration at the 2-position of the azetidine, pyrrolidine or piperidine ring, as represented by formula (IA):

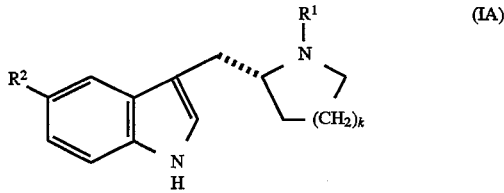

Also included in the invention are radiolabelled derivatives of compounds of formula (I) which are suitable for biological studies.

The pharmaceutically acceptable salts of the compounds of formula (I) are, for example, non-toxic acid addition salts formed with inorganic acids such as hydrochloric, hydrobromic, sulphuric and phosphoric acid, with organocarboxylic acids, or with organo-sulphonic acids. For a review of suitable pharmaceutical salts, see J. Pharm. Sci., 1977, 66, 1–19.

A preferred group of compounds of formula (I) is that wherein $R^1$ is $(R^3CO)C_1$–$C_2$ alkylene; $(R^4O_2C)$ $C_1$–$C_2$ alkylene; $(R^5R^6NOC)$ $C_1$–$C_2$ alkylene; $R^5R^6NO_2SCH_2CH_2$; $[R^3S(O)_m]C_1$–$C_2$ alkylene; $(R^7O)C_2$–$C_3$ alkylene; $(C_3$–$C_7$ cycloalkyl)$CH_2$; (phenyl) $C_1$–$C_2$ alkylene; (pyridyl) $C_1$–$C_2$ alkylene; $C_5$–$C_6$ cycloalkyl optionally substituted with HO;

$C_3$–$C_5$ alkenyl optionally substituted with phenyl; or cyclohexenyl; $R^2$ is $R^9NHOC$; $(R^9NHOC)C_1$–$C_2$ alkylene; $R^9NHO_2S$; $(R^9NHO_2S)$ $C_1$–$C_2$ alkylene; $R^{10}SO_2$; $(R_{10}SO_2)$ $C_1$–$C_2$ alkylene; $R_{12}CONH$; $(R^{12}CONH)C_1$–$C_2$ alkylene; $R^{10}SO_2NH$; $(R^{10}SO_2NH)C_1$–$C_2$ alkylene; or $R^{13}CH$=$CH$; $R^3$ is $C_1$–$C_6$ alkyl or aryl; $R^4$ is $C_1$–$C_6$ alkyl or (aryl)$C_1$–$C_3$ alkylene; $R^5$ and $R^6$ are each independently selected from H or $C_1$–$C_6$ alkyl; $R^7$ is H or $C_1$–$C_6$ alkyl; k is 1; m is 1 or 2; and $R^9$, $R^{10}$, $R^{12}$ and $R^{13}$ are as previously defined for formula (I).

A more preferred group of compounds of formula (I) is that wherein $R^1$ is $R^3COCH_2$; $R^3COCH_2CH_2$; $R^4O_2CCH_2$; $R^4O_2CCH_2CH_2$; $R^5R^6NOCCH_2$; $R^5R^6NOCCH_2CH_2$; $R^5R^6NOCCH(CH_3)$; $R^5R^6NO_2SCH_2CH_2$; $R^3S(O)_mCH_2CH_2$; $R^7OCH_2CH_2$; $R^7OCH(CH_3)CH_2$; $R^7OCH_2CH_2CH_2$; cyclopropyl$CH_2$; cyclobutyl$CH_2$; cyclopentyl$CH_2$; benzyl; phenyl$CH_2CH_2$; phenyl($CH_3$); pyridyl$CH_2$; pyridyl$CH_2CH_2$; cyclopentyl; hydroxycyclopentyl; allyl; pentenyl; cinnamyl; or cyclohexenyl; $R^2$ is $R^{10}SO_2CH_2CH_2$ or $R^9NHO_2SCH$=$CH$; $R^3$ is methyl or phenyl; $R^4$ is $(CH_3)_3C$ or benzyl; $R^5$ and $R^6$ are each independently selected from H or methyl; $R^7$ is H or methyl; $R^9$ is H or $C_1$–$C_6$ alkyl; $R^{10}$ is $C_1$–$C_6$ alkyl or aryl; k is 1; and m is 1 or 2.

A particularly preferred group of compounds of formula (I) is that wherein $R^1$ is $CH_3COCH_2CH_2$; $(CH_3)_3CO_2CCH_2CH_2$; benzyl$O_2CCH_2$; $H_2NOCCH_2CH_2$; $CH_3NHOCCH_2CH_2$; $(CH_3)_2NOCCH_2CH_2$; $H_2NO_2SCH_2CH_2$; phenyl$SOCH_2CH_2$; $HOCH_2CH_2$; $CH_3OCH_2CH_2$; cyclopropyl$CH_2$; cyclobutyl$CH_2$; cyclopentyl $CH_2$; phenyl$CH(CH_3)$; 2-pyridyl$CH_2$; 4-pyridyl$CH_2$; 2-pyridyl$CH_2CH_2$; cyclopentyl; 2-hydroxycyclopentyl; allyl; 3-methyl-2-butenyl; cinnamyl; or 3-cyclohexenyl; $R^2$ is $CH_3CH_2SO_2CH_2CH_2$; phenyl$SO_2CH_2CH_2$ or $H_2NO_2SCH$=$CH$; and k is 1.

In another aspect, the present invention provides processes for the preparation of compounds of formula (I) and their pharmaceutically acceptable salts.

A compound of formula (I) may be obtained by selective N-alkylation of the saturated heterocyclic ring of a compound of formula (II):

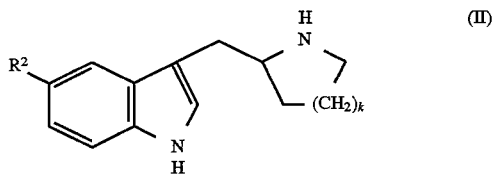

wherein $R^2$ and k are as previously defined for formula (I), using one or more of the following methods.

1. By reaction of a compound of formula (II) with a compound of formula $R^1X$, wherein $R^1$ is as defined for formula (I), and X is a suitable leaving group, e.g. halo (preferably chloro, bromo or iodo), $C_1$–$C_4$ alkanesulphonyloxy, trifluoromethanesulphonyloxy or arylsulphonyloxy (preferably benzenesulphonyloxy or p-toluenesulphonyloxy), in the presence of an appropriate base, e.g. sodium or potassium carbonate or bicarbonate, or triethylamine, in a suitable solvent such as a $C_1$–$C_4$ alkanol, 1,2-dimethoxyethane, acetonitrile, dimethylformamide or N,N-dimethylacetamide, and optionally in the presence of sodium or potassium iodide. The reaction can be conducted at from about 0° C. to about 150° C., preferably at from about room temperature to about 100° C.

2. By reductive alkylation of a compound of formula (II) using the appropriate aldehyde-, ketone- or carboxylic acid-containing $R^1$ precursor. In the case of an aldehyde or ketone precursor, the substrate (II) and carbonyl reagent may be reacted together under conventional catalytic hydrogenation conditions or in the presence of sodium cyanoborohydride, in a suitable solvent such as methanol or ethanol, at about room temperature. Alternatively, the reductive alkylation may be achieved by a two-step procedure in which the intermediate enamine is formed initially under conventional conditions and subsequently reduced to the required amine, e.g. using sodium cyanoborohydride in tetrahydrofuranmethanol at about room temperature.

In the case of a carboxylic acid precursor, the substrate (II) and the said acid reagent may be reacted together in the presence of excess sodium borohydride in a suitable solvent; preferably the carboxylic acid itself is used as solvent whenever possible. Since this reductive alkylation proceeds via in situ formation of the corresponding sodium triacyloxyborohydride, obvious variations are to employ preformed intermediate when commercially available or to preform it in a separate in situ step using the stoichiometric amount of carboxylic acid in a suitable solvent. An example of the latter procedure involves the treatment of six equivalents of the carboxylic acid with two equivalents of sodium borohyride in dry tetrahydrofuran at about room temperature. When formation of the required sodium triacyloxyborohydride is complete, the reaction mixture is treated with a solution of one equivalent of the substrate (II) in the same solvent and the subsequent reaction step is conducted at from about room temperature to about 70° C., preferably 50°–55° C.

3. When $R^1$ is $C_2$–$C_4$ alkyl or $C_3$–$C_7$ cycloalkyl, each substituted at the 2-position with a hydroxy group, by reaction of a compound of formula (II) with the appropriate epoxide-containing $R^1$ precursor, optionally in the presence of a tertiary amine base, e.g. triethylamine, and preferably in a suitable solvent such as $C_1$–$C_4$ alkanol. The reaction can be conducted at from about 0° C. to about 150° C., preferably at from about room temperature to about 60° C.

When $R^1$ is 2-hydroxyethyl, an "ethylene oxide equivalent" is preferably employed. Thus a compound of formula (II) may be reacted with ethylene carbonate in a suitable solvent such as dimethylformamide at about 120° C.

4. When $R^1$ is $C_2$–$C_4$ alkyl substituted at the 2-position with an electron withdrawing group such as $R^3CO$, $R^4O_2C$, $R^5R^6NOC$, $R^5R^6NO_2S$, $R^3SO$, $R^3SO_2$ and certain aryl and heteroaryl systems (e.g. 2- or 4-pyridyl), by conjugate addition (Michael-type reaction) of a compound of formula (II) to the corresponding α,β-unsaturated ketone-, ester-, amide-, sulphonamide-, sulphoxide-, sulphone-, arene- or heteroarene-containing $R^1$ precursor respectively, wherein $R^3$, $R^4$, $R^5$ and $R^6$ are as defined for formula (I), optionally in the presence of a tertiary amine base such as triethylamine. The reaction may optionally be conducted in a suitable solvent, e.g. N,N-dimethylacetamide, at from about 0° C. to about 100° C., preferably at about 100° C.

5. Certain compounds of formula (I) can be prepared from other compounds of formula (I) by, for example, the following conventional functional group transformations within the $R^1$ substituent:

(a) a compound of formula (I) wherein $R^1$ contains a $R^5R^6NOC$ substituent is obtainable from a corresponding ester of formula (I), i.e. wherein $R^1$ contains a $R^4O_2C$ substituent, by direct amination using an amine of formula $R^5R^6NH$. The reaction is preferably carried out using an excess of the amine in a suitable solvent such as a $C_1$–$C_4$ alkanol at an elevated temperature, e.g. the reflux temperature of the reaction medium. For low boiling amines, the reaction is preferably conducted in a sealed vessel.

The same over-all transformation can be effected indirectly via the intermediacy of the corresponding carboxylic acid, i.e. a compound of formula (I) wherein $R^1$ contains a $HO_2C$ substituent. Depending on the nature of the ester, its deprotection may be achieved by acid or alkaline hydrolysis, protonolysis (e.g. when $R^4$ is t-butyl) or hydrogenolysis (e.g. when $R^4$ is benzyl). Conversion of the acid to the required amide may also be achieved by a variety of methods. For example, the acid may be activated by formation of the corresponding acyl halide, e.g. bromide or chloride, followed by reaction of the latter with an amine of formula $R^5R^6NH$ optionally in the presence of a reaction-inert base to act as acid scavenger. Alternatively, any of a host of standard amide bond-forming (peptide coupling) reagents may be used. For example, the acid may be activated using a carbodiimide such as 1-ethyl-3-dimethylaminopropylcarbodiimide, optionally in the presence of 1-hydroxybenzotriazole and a reaction-inert amine such as N-methylmorpholine, followed by in situ reaction of the activated acid with an amine of formula $R^5R^6NH$;

(b) a compound of formula (I) wherein $R^1$ contains a $R^3SO$ or $R^3SO_2$ substituent is obtainable from the corresponding sulphide of formula (I), i.e. wherein $R^1$ contains a $R^3S$ substituent, either by controlled oxidation using a stoichiometric amount of oxidising agent, or by using the required excess of oxidising agent, respectively. Suitable oxidising agents are, for example, a peracid such as meta-chloroperbenzoic acid, hydrogen peroxide or nitronium tetrafluoroborate.

Certain compounds of formula (I) are preparable from other compounds of formula (I) by conventional functional group transformations within the $R^2$ substituent also. For example, the procedures outlined in 5(b) above for $R^1$ may be applied to $R^2$, such that $R^{10}S$ may be converted into either $R^{10}SO$ or $R^{10}SO_2$.

Other possibilities are as follows:

(c) a compound of formula (I) wherein $R^2$ is, or contains, a $H_2NOC$ substituent is obtainable from the corresponding nitrile of formula (I), i.e. wherein $R^2$ is, or contains, a NC substituent, by controlled hydrolysis, e.g. using sulphuric acid, boron trifluoride or potassium hydroxide, or via a corresponding imino ether derivative.

(d) a compound of formula (I) wherein $R^2$ is, or contains, a $R^{10}SO_2N(R^{11})$, $R^8R^9NOCN(R^{11})$ or $R^{10}O_2CN(R^{11})$ substituent is obtainable from the corresponding amide of formula (I), i.e. wherein $R^2$ is, or contains, a $R^{12}CON(R^{11})$ substituent. This may be achieved by hydrolysis of the amide to the corresponding amine using standard conditions, followed by reaction of the latter with, respectively, (i) a sulphonyl halide (preferably chloride) of formula $R^{10}SO_2$halo or a sulphonic anhydride of formula $(R^{10}SO_2)_2O$, or (ii) a carbamoyl chloride of formula $ClCONR^8R^9$ or, when $R^8$ is H, an isocyanate of formula $R^9NCO$ or, when both $R^8$ and $R^9$ are H, an inorganic isocyanate such as potassium isocyanate in the presence of an acid, e.g. acetic acid, or (iii) a chloroformate of formula $ClCO_2R^{10}$. The sulphonylations, and the acylations not involving an isocyanate, are optionally carried out in the presence of a reaction-inert base to act as acid scavenger.

(e) a compound of formula (I) wherein $R^2$ is $R^{13}CH_2CH_2$ may be obtained from the corresponding alkene of formula (I) wherein $R^2$ is $R^{13}(CH_2)_nCH=CH$, wherein n=0, by conventional catalytic or catalytic transfer hydrogenation, preferably using palladium as catalyst and, in the latter process, ammonium formate as the hydrogen source.

A compound of formula (II) may be obtained from a compound of formula (III):

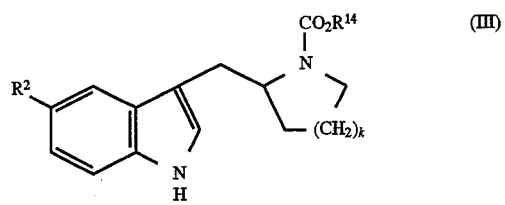

wherein $R^2$ and k are as previously defined for formula (II) and $R^{14}$ forms part of a conventional amino acid N-protecting group, i.e. a carbamate, wherein $R^{14}$ is preferably benzyl or t-butyl. N-Deprotection of a compound of formula (III) can be achieved using standard methodology; for example, when $R^{14}$ is benzyl, by palladium-catalysed hydrogenolysis and, when $R^{14}$ is t-butyl, by protonolysis using trifluoroacetic acid or hydrogen chloride.

Alternatively, when $R^{14}$ is benzyl, N-deprotection can be effected by modification of the procedure reported in Tetrahedron Letters, 1988, 29, 2983, in which (III) is treated with an excess of a tri(lower alkyl)silane in the presence of a palladium(II) salt and an excess of a tri(lower alkyl)amine in a suitable solvent such as a $C_1-C_4$ alkanol. Preferably the reaction is conducted using triethylsilane, palladium(II) acetate and triethylamine in ethanol at about room temperature.

Further useful non-hydrogenolytic N-deprotection procedures, when $R^{14}$ is benzyl, are either to employ hydrogen bromide in glacial acetic acid at about 0° C. or a Lewis acid-catalysed nucleophilic deprotection using, for example, boron trifluoride etherate and excess ethanethiol in a suitable solvent such as dichloromethane at about room temperature.

Depending on the nature of $R^2$, a compound of formula (III) can be obtained by a variety of synthetic methods.

1. For example, when $R^2$ is an ethyl group substituted at the 2-position with $R^8R^9NOC$, $R^8R^9NO_2S$, $R^{10}S(O)_m$, $R^{12}CON(R^{11})$, $R_{10}SO_2N(R^{11})$, $R^8R^9NOCN(R^{11})$ or $R^{10}O_2CN(R^{11})$, i.e. a compound of formula (III) wherein $R^2$ is $CH_2CH_2R^{13}$, wherein $R^{13}$ and m are as previously defined for formula (I), and $R^{14}$ and k are as previously defined for formula (III), by reduction of a compound of formula (IV):

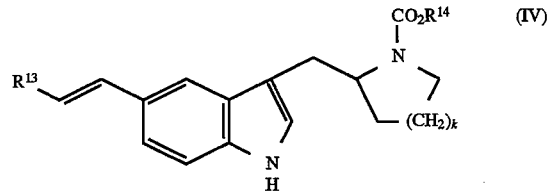

wherein $R^{13}$ is as previously defined for formula (I), and $R^{14}$ and k are as previously defined for formula (III). This may be achieved by conventional catalytic or catalytic transfer hydrogenation, preferably using palladium as catalyst and, in the latter case, ammonium formate as the hydrogen source.

Clearly, when $R^{14}$ is benzyl, a compound of formula (IV) may be converted directly to a compound of formula (II) wherein $R^2$ is $CH_2CH_2R^{13}$ under these conditions. Alternatively, when $R^{14}$ is t-butyl, a compound of formula (IV) may be converted to a compound of formula (II) wherein $R^2$ is $CH=CHR^{13}$ using the protonolysis conditions previously mentioned.

A compound of formula (IV) may be obtained from a compound of formula (V):

(V)

[Structure V: indole with Y substituent, CH₂-CH(CO₂R¹⁴)-N ring with (CH₂)ₖ]

wherein Y is chloro, bromo or iodo (preferably bromo), and R¹⁴ and k are as previously defined for formula (IV), with an alkene of formula $CH_2=CHR^{13}$, wherein $R^{13}$ is as previously defined for formula (IV), using the Heck reaction. Thus the desired coupling is achieved using, for example, an excess of the required alkene, in the presence of palladium(II) acetate, tri-o-tolylphosphine and triethylamine, in a suitable solvent such as acetonitrile or dimethylformamide, at from about 80° C. to about 160° C.

A compound of formula (V) may be obtained from a compound of formula (VI):

(VI)

[Structure VI]

wherein $R^{14}$, k and Y are as previously defined for formula (V), by selective and exhaustive reduction of the ketonic carbonyl group. This may be achieved using an alkali metal borohydride salt, preferably lithium borohydride, in a suitable solvent such as tetrahydrofuran, at from about room temperature to about 70° C.

A compound of formula (VI) may be obtained by acylating a suitably activated derivative of a compound of formula (VII):

(VII)

[Structure VII: indole with Y substituent]

wherein Y is as previously defined for formula (VI), with a suitably activated derivative of a compound of formula (VIII):

(VIII)

[Structure VIII]

wherein $R^{14}$ and k are as previously defined for formula (VI). Thus the N-protected α-amino acid of formula (VIII) is converted to the corresponding acyl bromide or chloride, preferably chloride, by standard methodology, e.g. using oxalyl chloride, optionally in the presence of a catalytic amount of dimethylformamide, in a suitable solvent such as dry dichloromethane; the indole of formula (VII) is converted to the corresponding 1-magnesium halide derivative by treatment with a $C_1$–$C_4$ alkyl magnesium halide, wherein halide means chloride, bromide or iodide, e.g. ethyl magnesium bromide, in a suitable solvent such as dry ether. The former acyl halide is then reacted with the latter 1-indolyl magnesium halide in a suitable solvent such as dry ether at from about –30° C. to about room temperature.

2. When $R^2$, $R^{14}$ and k are as previously defined for formula (III), the said compounds of formula (III) may be prepared by transition metal catalysed cyclisation of a compound of formula (IX):

(IX)

[Structure IX]

wherein $R^{15}$ is $OR^{14}$, $C_1$–$C_4$ alkyl, trifluoromethyl or phenyl, preferably trifluoromethyl, Z is chloro, bromo or iodo, preferably bromo or iodo, and $R^2$, $R^{14}$ and k are as previously defined for formula (III). For example, the reaction is conducted in the presence of an appropriate transition metal catalyst, e.g. palladium(II) acetate or tris (triphenylphosphine)rhodium(I) chloride, a phase transfer catalyst, e.g. a tetra($C_1$–$C_4$)alkylammonium halide, and a base, e.g. a tertiary amine such as triethylamine, in a suitable solvent such as dimethylformamide, at about 155° C.

A compound of formula (IX) may be obtained by the alkylation of a compound of formula (X):

(X)

[Structure X]

wherein $R^2$, $R^{15}$ and Z are as previously defined for formula (IX), with a compound of formula (XI):

(XI)

[Structure XI]

wherein $R^{14}$ and k are as previously defined for formula (IX), using the Mitsunobu coupling procedure, preferably with triphenylphosphine and diethyl azodicarboxylate as the required reagents, in a suitable solvent such as tetrahydrofuran at about room temperature.

A compound of formula (X) may be obtained by standard acylation of an amine of formula (XII):

(XII)

[Structure XII]

wherein $R^2$ and Z are as previously defined for formula (X), with a chloroformate of formula $R^{15}COCl$ or an acyl halide (preferably chloride) of formula $R^{15}COhalo$, wherein $R^{15}$ is as previously defined for formula (X), or with an acid anhydride of formula $(R^{15}CO)_2O$ wherein $R^{15}$ is as previously defined for formula (X) but is not $OR^{14}$.

A compound of formula (XI) may be obtained by selective reduction of the ester group of a compound of formula (XIII):

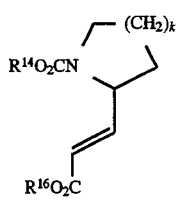

wherein $R^{16}$ is $C_1-C_4$ alkyl or benzyl, and $R^{14}$ and k are as previously defined for formula (XI), using, for example, diisobutylaluminiumhydride in a suitable solvent such as tetrahydrofuran at about −70° C.

A compound of formula (XIII) may be obtained by reacting an aldehyde of formula (XIV):

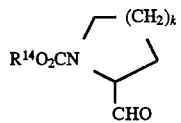

wherein $R^{14}$ and k are as previously defined or formula (XIII), either with a phosphonium salt of formula (XV) or with a phosphonate of formula (XVI):

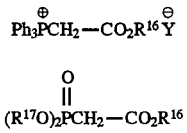

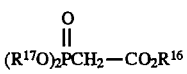

wherein $R^{17}$ is $C_1-C_4$ alkyl or phenyl, preferably methyl or ethyl, $R^{16}$ is as previously defined for formula (XIII), and Y is as previously defined for formula (V), using standard Wittig or Wittig-Horner reaction conditions.

It will be appreciated by persons skilled in the art that, within the various processes described, the order of the synthetic steps employed may be varied and will depend inter alia on factors such as the nature of other functional groups present in a particular substrate, the availability of key intermediates, and the protecting group strategy to be adopted (if any). Clearly, such factors will also influence the choice of reagent for use in said synthetic steps.

For example, an alternative approach to a compound of formula (I) wherein $R^2$ is an ethyl group substituted at the 2-position with $R^8R^9NOC$, $R^8R^9NO_2S$, $R^{10}S(O)_m$, $R^{12}CON(R^{11})$, $R^{10}SO_2N(R^{11})$, $R^8R^9NOCN(R^{11})$ or $R^{10}O_2CN(R^{11})$, i.e. a compound of formula (I) wherein $R^2$ is $CH_2CH_2R^{13}$, wherein $R^{13}$ is as previously defined for formula (I), and $R^1$ and k are also as previously defined for formula (I), involves the reaction of a compound of formula (I) wherein $R^2$ is Y, wherein Y is as previously defined for formula (V), and $R^1$ and k are as previously defined for formula (I), with an alkene of formula $CH_2=CHR^{13}$ wherein $R^{13}$ is as defined above, under the Heck reaction conditions previously described for the conversion of (V) to (IV), optionally followed by hydrogenation of the product as in the conversion of (IV) to (III).

A compound of formula (I) wherein $R^2$ is Y, wherein Y is as previously defined for formula (V), and $R^1$ and k are as previously defined for formula (I), may be obtained by selective N-alkylation of a compound of formula (II) wherein $R^2$ is Y, wherein Y is as previously defined for formula (V), and k is as previously defined for formula (I), by analogy with the procedures described earlier for the conversion of (II) to (I).

A compound of formula (II) wherein $R^2$ is Y, wherein Y is as previously defined for formula (V), and k is as previously defined for formula (I), may be obtained from a compound of formula (V) wherein $R^{14}$, k and Y are as previously defined for formula (V) by the standard N-deprotection methodology already described for the conversion of (III) to (II). Preferably however, when $R^{14}$ is benzyl, deprotection is effected by a non-hydrogenolytic procedure.

Compounds of formulae (VII), (VIII), (XII), (XIV), (XV) and (XVI), and the various reagents required for the processes hereinbefore disclosed, when neither commercially available nor subsequently described, can be obtained either by analogy with the reactions described in the Examples and Preparations sections or by conventional synthetic procedures, in accordance with standard textbooks on organic chemistry or literature precedent, from readily accessible starting materials using appropriate reagents and reaction conditions. Clearly, when the preferred stereoisomers of formula (IA) are required, the compounds of formulae (VIII) and (XIV) will possess the 2R-configuration.

Persons skilled in the art will recognise that the alkenes depicted hereinbefore may be obtained in cisor trans-stereoisomeric forms, or as mixtures of cis- and trans-stereoisomers, and are represented in one such form only in the interests of clarity and convenience. Such persons will also be aware of variations of, and alternativesto, those reactions described hereinafter for the preparation of compounds of formula (I).

The pharmaceutically acceptable acid addition salts of compounds of formula (I) may also be prepared in a conventional manner. For example a solution of the free base is treated with the appropriate acid, either neat or in an appropriate solvent, and the resulting salt isolated either by filtration or by evaporation under vacuum of the reaction solvent. Certain such salts may be formed or interconverted using ion-exchange resin techniques.

The compounds of the invention are selective agonists at the "5-$HT_1$-like" subtype of the 5-HT (serotonin) receptor and are therefore useful in the curative or prophylactic treatment of migraine and associated conditions such as cluster headache, chronic paroxysmal hemicrania and headache associated with vascular disorders. Certain of these compounds are also agonists at central 5-$HT_1$ receptors and are therefore useful for the treatment of depression, anxiety, eating disorders, obesity and drug abuse.

The in vitro evaluation of the "5-$HT_1$-like" receptor agonist activity of the compounds of the invention is carried out by testing the extent to which they mimic sumatriptan in contracting the isolated dog saphenous vein strip (P. P. A. Humphrey et al., Brit. J. Pharmacol., 1988, 94, 1123). This effect can be blocked by methiothepin, a known 5-HT antagonist. Sumatriptan is known to be useful in the treatment of migraine and produces a selective increase in carotid vascular resistance in the anaesthetized dog and a consequent decrease in carotid arterial blood flow. It has been suggested (W. Feniuk et al., Brit. J. Pharmacol., 1989, 96, 83) that this is the basis of its efficacy.

The 5-$HT_1$ agonist activity of the compounds of the invention can be measured in in vitro receptor binding assays as described for the 5-$HT_{1A}$ receptor, using rat cortex as the receptor source and [$^3$H]8-OH-DPAT as the radioligand (D. Hoyer et al., Europ. J. Pharmacol., 1985, 118, 13), and as described for the 5-$HT_{1D}$ receptor, using bovine caudate as the receptor source and [$^3$H]5-HT as the radioligand (R. E. Heuring and S. J. Peroutka, J. Neuroscience, 1987, 7, 894).

In therapy, the compounds of formula (I) and their pharmaceutically acceptable salts can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavouring or colouring agents. They can also be injected parenterally, for example, intravenously, intramuscularly or subcutaneously. For parenteral administration, they are best used in the form of a sterile aqueous solution which may contain other substances, for example, enough salts or glucose to make the solution isotonic with blood. For buccal or sublingual administration they may be administered in the form of tablets or lozenges which can be formulated in a conventional manner.

For oral, parenteral, buccal and sublingual administration to patients, the daily dosage level of the compounds of formula (I) and their pharmaceutically acceptable salts will be from 0.01 to 20 mg/Kg (in single or divided doses). Thus tablets or capsules will contain from 5 mg to 0.5 g of active compound for administration singly, or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the compounds of formula (I) and their pharmaceutically acceptable salts can be administered in the form of a suppository or pessary, or they may be applied topically in the form of a lotion, solution, cream, ointment or dusting powder. For example, they can be incorporated into a cream consisting of an aqueous emulsion or polyethylene glycols or liquid paraffin; or they can be incorporated, at a concentration of from 1 to 10%, into an ointment consisting of a white wax or white soft paraffin base together with such stabilisers and preservatives as may be required.

The compounds of formula (I) and their pharmaceutically acceptable salts can also be administered intranasally or by inhalation and are conveniently delivered in the form of a solution or suspension from a pump spray container, which is squeezed or pumped by the patient, or as an aerosol spray presentation from a pressurised container or a nebuliser with the use of a suitable propellant, e.g. dichlorodifluoromethane, trichlorofluoromethane, dichlorotetrafluoroethane, carbon dioxide or other suitable gas. In the case of a pressurised aerosol, the dosage unit may be determined by providing a valve to deliver a metered amount. The pressurised container or nebuliser may contain a solution or suspension of the active compound. Capsules and cartridges (made, for example, from gelatin) for use in an inhaler or insufflator may be formulated containing a powder mix of a compound of the invention and a suitable powder base such as lactose or starch.

Aerosol formulations are preferably arranged so that each metered dose or "puff" of aerosol contains from 20 µg to 1000 µg of a compound of formula (I), or a pharmaceutically acceptable salt thereof, for delivery to the patient. The overall daily dose with an aerosol will be within the range of from 100 µg to 10 mg which may be administered in a single dose or, more usually, in divided doses throughout the day.

Thus the invention provides pharmaceutical compositions comprising a compound of formula (I), or a pharmaceutically acceptable salt thereof, together with a pharmaceutically acceptable diluent or carrier.

The invention also provides a compound of formula (I), or a pharmaceutically acceptable salt thereof, or a pharmaceutical composition containing either entity, for use in medicine.

The invention further includes the use of a compound of formula (I), or a pharmaceutically acceptable salt thereof, or a pharmaceutical composition containing either entity, both for the manufacture of a medicament for the curative or prophylactic treatment of migraine or an associated condition such as cluster headache, chronic paroxysmal hemicrania or headache associated with a vascular disorder, or of depression, anxiety, an eating disorder, obesity or drug abuse, and also for the manufacture of a medicament for the curative or prophylactic treatment of a medical condition for which a selective agonist of $5\text{-HT}_1$-like receptors is indicated.

In a further aspect, the invention provides both a method of treating a human being to cure or prevent migraine or an associated condition such as cluster headache, chronic paroxysmal hemicrania or headache associated with a vascular disorder, or depression, anxiety, an eating disorder, obesity or drug abuse, and also a method of treating a human being to cure or prevent a medical condition for which a selective agonist of $5\text{-TH}_1$-like receptors is indicated, which comprises treating said human being with an effective amount of a compound of formula (I), or a pharmaceutically acceptable salt thereof, or a pharmaceutical composition containing either entity.

The invention also includes any novel intermediates of formula (II) disclosed herein.

The syntheses of the compounds of the invention and of the intermediates for use therein are illustrated by the following Examples and Preparations. The purity of the compounds was routinely monitored by thin layer chromatography (Rf) using Merck Kieselgel 60 $F_{254}$ plates and the following solvent systems (SS):

1. dichloromethane;
2. dichloromethane:ethanol:0.880 aqueous ammonia, 90:10:1;
3. hexane:ethyl acetate, 1:1;
4. dichloromethane:methanol:0.880 aqueous ammonia, 90:10:1;
5. methanol;
6. ethyl acetate:diethylamine, 95:5;
7. dichloromethane:methanol:0.880 aqueous ammonia, 90:10:0.5.

$^1$H Nuclear magnetic reasonance (NMR) spectra were recorded using either a Nicolet QE-300 or a Bruker AC-300 spectrometer and were in all cases consistent with the proposed structures- Chemical shifts ($\delta$) are given in parts-per-million downfield from tetramethylsilane using conventional abbreviations for designation of major peaks: s, singlet; d, doublet; dd, doublet of doublets; t, triplet; m, multiplet; br, broad. LRMS means low resolution mass spectrum. Room temperature means 20°–25° C.

EXAMPLE 1

5-(2-Ethylsulphonylethyl)-3-[N-[2-pyridylmethyl)-2(R)-pyrrolidinylmethyl]-1H-indole To a stirred solution of 5-(2-ethylsulphonylethyl)-3-(2(R)-pyrrolidinylmethyl)-1H-indole (Preparation 5; 150 mg, 0.47 mmol) in dry dimethylformamide (4 ml) at room temperature under nitrogen were added, sequentially, anhydrous sodium carbonate (110 mg, 1.04 mmol), 2-pyridylmethyl chloride hydrochloride (85 mg, 0.52 mmol) and sodium iodide (10 mg). The resulting mixture was heated at 100° C. for 18 hours, then allowed to cool to room temperature. It was then partitioned between ethyl acetate and water, and the organic phase separated, washed with water (3×), dried ($Na_2SO_4$), and evaporated under reduced pressure to give an oil. Purification by column chromatography on silica gel, eluting with an ethanol in dichloromethane gradient (0 to 5% ethanol), afforded the title compound as a gum (62 mg). $[\alpha]_D^{25}$+22° (c=0.1, $CH_3OH$). Found: C,59.89; H,6.44; N,9.07. $C_{23}H_{29}N_3O_2S$; 0.75 $CH_2Cl_2$ requires C,60.02; H,6.47; N,8.84%. δ($CDCl_3$): 1.35 (3H,t), 1.50–1.90(4H,m), 2.30–2.40(1H,m), 2.65–2.75(1H, m), 2.90(3H,q and m), 3.00–3.20(2H,m), 3.20–3.30(4H,m), 3.60(1H,d), 4.28(1H,d), 5.30(1.5H,s,$CH_2Cl_2$), 7.02(1H,d), 7.05(1H,s), 7.16–7.20(1H,dd), 7.30(1H,d), 7.40(1H,s), 7.50 (1H,d), 7.70(1H,dd), 8.14(1H,br s), 8.58(1H,d).

The following twenty seven compounds were obtained from Preparations 5, 6 or 7, employed either as the free base or hydrochloride salt, using an appropriate alkylating agent, the required amount of acid scavenger, and a suitable solvent such as dimethylformamide, N,N-dimethylacetamide or 1,2-dimethoxyethane, by procedures similar to that described in Example 1.

EXAMPLE 2

3-(N-Benzyl-2(R)-pyrrolidinylmethyl)-5-(2-ethylsulphonylethyl)-1H-indole

Obtained as a gum, using preparation 5 and benzyl bromide- Rf 0.70 (SS 2). $[\alpha]_D^{25}$+33° (c=0.1, $CH_3OH$). Found: C,66.87; H,7.10; N,6.57. $C_{24}H_{30}N_2O_2S$; 0.125 $H_2O$; 0.25 $CH_2Cl_2$ requires C,67.10; H,7.14; N,6.45%. δ($CDCl_3$): 1.35(3H,t), 1.50–1.90(4H,m), 2.25(1H,m), 2.65–3.40(9H, m), 2.90(2H,q), 4.15(1H,d), 5.30(0.5H,s,$CH_2Cl_2$), 7.00(1H, d), 7.05(1H,s), 7.25–7.40(7H,m), 8.00(1H,br s).

EXAMPLE 3

3-(N-Allyl-2(R)-pyrroldinylmethyl)-5-(2-ethylsulphonylethyl)-1H-indole

Obtained as a gum, using preparation 5 and allyl bromide. Rf 0.70 (SS 2). $[\alpha]_D^{25}$+53° (c=0.1, $CH_3OH$). Found: C, 63.98; H, 7.92; N, 7.48. $C_{20}H_{28}N_2O_2S$; 0.50 $H_2O$; 0.125 $CH_2Cl_2$ requires C,63.58; H,7.75; N,7.37%. δ($CDCl_3$): 1.38 (3H,t), 1.50–1.90(4H,m), 2.20–2.35(1H,m), 2.60–2.80(2H, m), 2.90–3.00(3H,m), 3.10–3.40(6H,m), 3.65(1H,dd), 5.15 (1H,d), 5.25(1H,d), 5.30(0.25H,s, $CH_2Cl_2$), 5.95–6.10(1H, m), 7.05(1H,d), 7.08(1H,s), 7.30(1H,d), 7.42(1H,s), 8.05 (1H,br s).

EXAMPLE 4

5-(2-Ethylsulphonylethyl)-3-[N-(2-methoxyethyl)-2-(R)-pyrrolidinylmethyl]-1H-indole Obtained as a gum, using preparation 5 and 2-methoxyethyl bromide. Rf 0.35 (SS 2). $[\alpha]_D^{25}$+49° (c=0.1, $CH_3OH$). Found: C,58.81; H,7.45; N,6.58. $C_{20}H_{30}N_2O_3S$; 0.50 $CH_2Cl_2$ requires C,58.48; H,7.42; N,6.65%. δ($CDCl_3$): 1.38(3H,t), 1.50–1.90(4H,m), 2.20–2.35(1H,m), 2.45–2.55 (1H,m), 2.60–2.80(2H,m), 2.92(2H,q), 3.10–3.35(7H,m), 3.40(3H,s), 3.65–3.70(2H,m), 5.30(1H,s,$CH_2Cl_2$), 7.04(1H, d), 7.08(1H,s), 7.30(1H,d), 7.45(1H,s), 8.05(1H,br s).

EXAMPLE 5

5-(2-Ethylsulphonylethyl)-3-[N-(2-oxopropyl)-2-(R)-pyrrolidinylmethyl]-1H-indole Obtained as a gum, using Preparation 5 and chloroacetone. Rf 0.60 (SS 4). $[\alpha]_D^{25}$+28° (c=0.1, $CH_3OH$). Found: C,62.41; H,7.40; N,7.20. $C_{20}H_{28}N_2O_3S$; 0.10 $CH_2Cl_2$ requires C,62.70; H,7.38; N,7.28%. δ($CDCl_3$): 1.38(3H,t), 1.50–1.90(4H,m), 2.15(3H,s), 2.20–2.30(1H,m), 2.68–2.75 (1H,m), 2.80–3.08(5H,m), 3.15(1H,d), 3.20–3.38(4H,m), 3.68(1H,d), 5.30(0.20H,s,$CH_2Cl_2$), 7.02(2H,m), 7.30(1H,d), 7.42(1H,s), 8.00(1H,br s).

EXAMPLE 6

3-(N-Cinnamyl-2(R)-pyrrolidinylmethyl)-5-(2-ethylsulphonylethyl)-1H-indole

Obtained as a foam, using Preparation 5 and cinnamyl bromide. Rf 0.80 (SS 4). $[\alpha]_D^{25}$−27° (c=0.1, $CH_3OH$). Found: C,63.73; H,6.66; N,5.78. $C_{26}H_{32}N_2O_2S$; $H_2O$; 0.50 $CH_2Cl_2$ requires C,64.02; H,6.49; N,5.64%. δ($CDCl_3$): 1.30 (3H,t), 1.70–2.08(4H,m), 2.60(1H,m), 2.84–2.95(3H,m), 3.10–3.50(8H,m); 3.68(1H,dd), 5.30(1H,s,$CH_2Cl_2$), 6.28–6.38(1H,m), 6.48(1H,d), 7.00(1H,d), 7.18–7.35(7H, m), 7.42(1H,s), 8.62(1H,br s).

EXAMPLE 7

3-[N-(3-Cyclohexenyl)-2(R)-pyrrolidinylmethyl]-5-(2-ethylsulphonylethyl)-1H-indole Obtained as a foam, using Preparation 5 and 3-bromocyclohexene. Rf 0.70 (SS 4). $[\alpha]_D^{25}$+3° (c=0.1, $CH_3OH$). Found: C,64.33; H,7.51; N,6.76. $C_{23}H_{32}N_2O_2S$; 0.25 $H_2O$; 0.33 $CH_2Cl_2$ requires C,64.66; H,7.71; N,6.46. δ($CDCl_3$): 1.38(3H,t), 1.50–2.30(11H,m), 2.80–3.00(3H,m), 3.10–3.60(7H,m), 3.70–3.84(1H,m), 5.30(0.67H,s,$CH_2Cl_2$), 5.68–6.10(2H,m), 7.05(1H,d), 7.20(1H,br s), 7.34(1H,d), 7.42(1H,s), 8.22(1H,br s).

EXAMPLE 8

5-(2-Ethylsulphonylethyl)-3-[N-(3-methyl-2-butenyl)-2(R)-pyrrolidinylmethyl]-1H-indole Obtained as a gum, using Preparation 5 and 3-methyl-2-butenyl bromide. Rf 0.55 (SS 4). $[\alpha]_D^{25}$+36° (c=0.1, $CH_3OH$). Found: C,64.72; H,8.05; N,6.91. $C_{22}H_{32}N_2O_2S$; 0.50 H20; 0.14 $CH_2Cl_2$ requires C,64.91; H,8.19; N,6.84. δ($CDCl_3$): 1.38(3H,t), 1.50–1.90(10H,m), 2.30(1H,m), 2.75 (1H,m), 2.90–3.02(4H,m), 3.10–3.35(6H,m), 3.55(1H,m), 5.38(1H, br t), 7.00–7.10(2H,m), 7.30(1H,d), 7.42(1H,s), 8.00(1H, br s).

EXAMPLE 9

3-(N-Cyclopentyl-2(R)-pyrrolidinylmethyl)-5-(2-ethylsulphonylethyl)-1H-indole

Obtained as a foam, using Preparation 5 and cyclopentyl iodide. Rf 0.36 (SS 4). $[\alpha]_D^{25}$+29° (c=0.1, $CH_3OH$). Found: C,64.28; H,7.80; N,6.40. $C_{22}H_{32}N_2O_2S$; 0.80 $H_2O$; 0.10 $CH_2Cl_2$ requires C,64.49; H,8.27; N,6.81%. δ($CDCl_3$): 1.38 (3H,t), 1.50–2.10(12H,m), 2.60–2.90(2H,m), 2.90(2H,q), 3.10–3.50(8H,m), 5.30(0.20H,s,$CH_2Cl_2$), 7.04(1H,d), 7.10 (1H,s), 7.32(1H,d), 7.40(1H,s), 8.18(1H,br s).

EXAMPLE 10

3-(N-Cyclopropylmethyl-2(R)-pyrrolidinylmethyl)-5-(2-ethylsulphonylethyl)-1H-indole Obtained as a foam, using Preparation 5 and cyclopropylmethyl bromide. Rf 0.44 (SS 4). $[\alpha]_d^{25}$+47° (c=0.1, $CH_3OH$). Found: C,65.05; H,8.27; N,7.27. $C_{21}H_{30}N_2O_2S$; 0.40 $H_2O$; 0.05 $CH_2Cl_2$ requires C,65.34; H,8.05; N,7.24%. δ($CDCl_3$): 0.22(2H,m), 0.60(2H,m), 1.05(1H,m), 1.38(3H, t), 1.96–2.55(4H,m), 2.10(1H,m), 2.38(1H,m), 2.78 (1H,m), 2.90–3.05(4H,m), 3.15–3.35 (5H,m), 3.52(1H,m), 5.30 (0.10H, s, $CH_2Cl_2$), 7.04(1H,d), 7.10 (1H,br s), 7.30(1H,d), 7.40(1H,s), 8.05 (1H, br s).

EXAMPLE 11

3-(N-Carbamoylmethyl-2(R)-pyrrolidinylmethyl)-5-(2-ethylsulphonylethyl-1H-indole Obtained as a foam, using preparation 5 and 2-bromoacetamide. Rf 0.50 (SS 4). $[\alpha]_D^{25}$+25° (c=0.1, $CH_3OH$). Found: C,58.94; H,6.81; N,10.70. $C_{19}H_{27}N_3O_3S$; 0.17 CHlCl2 requires C,58.77; H,7.03; N,10.73%. ($CDCl_3$): 1.40(3H,t), 1.50–1.95(5H,m), 2.35(1H,m), 2.70(1H,m), 2.85–3.00(4H,m), 3.10–3.35(5H,m), 3.42(1H,d), 5.30 (0.33H,s,$CH_2Cl_2$), 5.55(1H,br s), 6.98(1H,s), 7.04(1H,d), 7.10(1H,br s), 7.30(1H,d), 7.60(1H,s), 8.10(1H, br s).

EXAMPLE 12

5-(2-Ethylsulphonylethyl)-3-[N-(4-pyridylmethyl)-2(R)-pyrroldinylmethyl]-1H-indole Obtained as a gum, using preparation 5 and 4-pyridylmethyl chloride hydrochloride. Rf 0.75 (SS 4). $[\alpha]_D^{25}$+13° (c=0.1,$CH_3OH$). Found: C,59.60; H,6.45; N,9.00. $C_{23}H_{29}N_3O_2S$; 0.80 $CH_2Cl_2$ requires C,59.61; H.6.43; N, 8.76%. δ($CDCl_3$): 1.35(3H,t), 1.55–1.92(5H,m), 2.20(1H,m), 2.70–3.25(5H,m), 3.28(4H,s), 3.35(1H,d), 4.15 (1H,d), 5.30(1.60H,s,$CH_2Cl_2$), 7.12–7.18(2H,m), 7.32(3H, m), 7.40(1H,s), 8.15(1H,br s), 8.55(2H,d).

EXAMPLE 13

5-(2-Ethylsulphonylethyl)-3-{N-(1(R,S)-phenylethyl]-2(R)-pyrrolidinylmethyl}-1H-indole Obtained as a foam, using Preparation 5 and α-methylbenzyl bromide. Rf 0.80 and 0.90 (SS 4), 0.30 and 0.40 (SS 5). $[\alpha]_D^{25}$–14° (c=0.1, $CH_3OH$). Found: C,69.15; H,7.44; N,6.42. $C_{25}H_{32}N_2O_2S$; 0.50 $H_2O$ requires C,69.25; H,7.67; N,6.46%. δ($CDCl_3$)—1:1 mixture of diastereoisomers: 1.30–2.00(10H,m), 2.40–2.90(3H,m), 2.90(2H, 2xq), 3.05–3.40(6H,m), 3.65 and 4.04(1H,m), 6.80–7.00(2H,m), 7.10–7.60(7H,m), 7.96 and 8.02(1H, br s).

EXAMPLES 13A AND 13B 5-(2-Ethylsulphonylethyl)-3-{N-[(R)-phenylethyl]-2(R)-pyrrolidinylmethyl}-1H-indole and
5-(2-Ethylsulphonylethyl)-3-{N-[1(S)-phenylethyl]-2(R)-pyrrolidinylmethyl}-1H-indole The mixture of diastereoisomers of Example 13 was resolved by conventional column chromatography on silica gel to afford the title compounds as diastereoisomer 1 and diastereoisomer 2. However, which diastereoisomer corresponds with which title compound was not established.
Diastereoisomer 1

Obtained as a foam. Rf 0.40 (SS 5). $[\alpha]_D^{25}$+33° (c=0.1, $C_3OH$). Found: C,69.60; H,7.40; N,6.85. $C_{25}H_{32}N_2O_2S$; 0.33 $H_2O$ requires C,69.73; H,7.64; N,6.51%. δ($CDCl_3$): 1.38(3H,t), 1.50–1.90(7H,m), 2.50–3.00(5H, q and m), 3.05–3.31(6H,m), 4.06(1H,m), 6.84–7.10(2H,m), 7.30(1H, m), 7.42(6H,m), 7.98(1H,br s).
Diastereoisomer 2

Obtained as a foam. Rf 0.30 (SS 5). $[D]_D^{25}$–53° (c=0.1, $CH_3OH$). Found: C,69.63; H,7.70; N,6.34. $C_{25}H_{32}N_2O_2S$; 0.33 $H_2O$ requires C,69.73; H,7.64; N,6.51%. δ($CDCl_3$): 1.30–1.90(10H, t and m), 2.30–3.00(5H, q and m), 3.10–3.20(6H,m), 3.68(1H,m), 6.90(1H,s), 6.95(1H,d), 7.25 (1H,m), 7.30–7.60(6H,m), 7.90(1H, br s).

EXAMPLE 14

5-(2-Ethylsulphonylethyl)-3-[N-(2-phenylethyl)-2(R)-pyrrolidinylmethyl]-1H-indole Obtained as a foam, using Preparation 5 and 2-phenylethyl iodide. Rf 0.83 (SS 4). $[\alpha]_D^{25}$+33° (c=0.1, $CH_3OH$). Found: C,68.39; H,7.55; N,6.30. $C_{25}H_{32}N_2O_2S$; 0.20 $CH_2Cl_2$ requires C,68.54; H,7.40; N,6.34% δ($CDCl_3$): 1.40(3H,t), 1.60–2.00(5H,m), 2.45(1H,m), 2.60(1H,m), 2.70–2.98(5H,m), 3.15–3.34(6H,m), 3.45(1H,m), 5.30 (0.40H,s,$CH_2Cl_2$), 7.05–7.10(2H,m), 7.15–7.36(6H,m), 7.45(1H,s), 8.08(1H,br s).

EXAMPLE 15

3-(N-Benzyloxycarbonylmethyl-2(R)-pyrrolidinylmethyl)-5-(2-ethylsulphonylethyl)-1H-indole Obtained as a gum, using Preparation 5 and benzyl bromoacetate. Rf 0.80 (SS 4). $[\alpha]_D^{25}$+30° (c=0.1, $CH_3OH$). Found: C,66.01; H,6.82; N,5.74. $C_{26}H_{32}N_2O_4S$; 0.25 $H_2O$ requires C,66.00; H,6.92; N,5.92%. δ($CDCl_3$): 1.36(3H,t), 1.44–2.04(5H,m), 2.64(1H,m), 2.80(1H,m), 2.92(2H,q), 3.02–3.44(7H,m), 3.70(1H,d), 5.10(2H,q), 7.03(1H,d), 7.10 (1H,br s), 7.22–7.40(6H,m), 7.42(1H,s), 7.94 (1H,br s).

EXAMPLES 16A AND 16B

3-{N-[1(R)-Carbamoylethyl]-2(R)-pyrrolidinylmethyl}-5-(2-ethylsulphonylethyl)-1H-indole and
3-{N-[1(S)-Carbamoylethyl]-2(R)-pyrrolidinylmethyl}-5-(2-ethylsulphonylethyl)-1H-indole The mixture of diastereoisomers obtained using Preparation 5 and 2-bromopropionamide was resolved by conventional column chromatography on silica gel to afford the title compounds as diastereoisomer 1 and diastereoisomer 2. However, which diastereoisomer corresponds with which title compound was not established.

Diastereoisomer 1

Obtained as a foam. Rf 0.55 (SS 4). $[\alpha]_D^{25}$+24° (c=0.1, $CH_3OH$). Found: C,59.56; H,7.42; N,10.18. $C_{20}H_{29}N_3O_3S$; 0.25 $H_2O$; 0.10 $CH_2Cl_2$ requires C,59.68; H,7.40; N,10.39%. δ($CDCl_3$): 1.24(3H,d), 1.35(3H,t), 1.52–1.90 (4H,m), 2.58–2.72(2H,m), 2.82(1H,m), 2.85–3.10(4H,m), 3.15–3.35(4H,m), 3.50(1H,q), 5.30(0.20H, $CH_2Cl_2$), 5.65 (1H,br s), 7.00–7.08(2H,m), 7.20(1H,br s), 7.28(1H,d), 7.40 (1H,s), 8.30(1H,br s).

Diastereoisomer 2

Obtained as a foam. Rf 0.50(SS 4). $[\alpha]_D^{25}$+26° (c=0.1, $CH_3OH$). Found: C,59.25; H,7.20; N,10.11$C_{20}H_{29}N_3O_3S$; 0.25 $CH_2Cl_2$ requires C,58.92; H,7.20; N,10.18%. δ($CDCl_3$): 1.35–1.40(6H,d and t), 1.56–1.85(4H,m), 2.56 (1H,m), 2.70(1H,m), 2.86–3.00(3H,m), 3.10(1H,m), 3.22–3.35(5H,m), 3.40(1H,q), 5.30(0.50H,s,$CH_2Cl_2$), 5.80 (1H,br s), 6.85(1H,br s), 6.96–7.02(2H,m), 7.30(1H,d), 7.40 (1H,d), 8.35(1H, br s).

EXAMPLE 17

5-(2-Ethylsulphonylethyl-3-[N-(3-methoxy-1-propyl)-2(R)-pyrrolidinylmethyl]-1H-indole Obtained as a foam, using preparation 5 and 3-methoxy-1-propyl bromide. Rf 0.47 (SS 4). $[\alpha]_D^{25}$+58° (C=0.1, $CH_3OH$). Found: C,62.78; H,8.25; N,6.99. $C_{21}H_{32}N_2O_3S$; 0.125 $CH_2Cl_2$ requires C, 62.92; H, 8.06; N,6.95%. δ($CDCl_3$): 1.40(3H,t), 1.55–1.95(6H,m), 2.24–2.45(2H,m), 2.65–2.85(2H,m), 2.96(2H,q), 3.08–3.38(10H,m), 3.50(2H, m), 5.30(0.25H,s,$CH_2Cl_2$), 7.05(1H,d), 7.10(1H,s), 7.35 (1H,d), 7.45(1H,s), 8.10 (1H,br s).

EXAMPLE 18

3-(N-Cyclobutylmethyl-2(R)-pyrolidinylmethyl)-5-(2-ethylsulphonylethyl)-1H-indole This compound was also prepared by an alternative procedure (b).

(a)

Obtained as a foam, using preparation 5 and cyclobutylmethylbromide. Rf 0.40 (SS 4). $[\alpha]_D^{25}$+25° (c=0.1, CH$_3$OH). Found: C,65.88; H,8.58; N,7.16. C$_{22}$H$_{32}$N$_2$O$_2$S; 0.10 CH$_2$Cl$_2$; 0.30 H$_2$O requires C,65.86; H,8.22; N,6.95%. δ(CDCl$_3$): 1.35(3H,t), 1.52–2.00(8H,m), 2.16–2.22(2H,m), 2.25–2.50(2H,m), 2.60–3.02(5H,m), 3.06–3.12(1H,m), 3.16–3.40(6H,m), 5.30(0.20H,s,CH$_2$Cl$_2$), 7.02(1H,d), 7.10 (1H,s), 7.32(1H,d), 7.44(1H,s), 8.35(1H,br s).

(b)

Sodium borohydride (76 mg, 2.0 mmol) was added in small portions to a stirred solution of cyclobutanecarboxylic acid (600 mg, 6.0 mmol) in dry tetrahydrofuran (10 ml) at room temperature under nitrogen- After 2.5 hours, when gas evolution had ceased, a solution of 5-(3-ethylsulphonylethyl)-3-(2(R)-pyrroldinylmethyl)-1H-indole (preparation 5; 320 mg, 1.0 mmol) in dry tetrahydrofuran (5 ml) was added and the resulting reaction mixture heated at 50°–55° C. for 2 days. The cool reaction mixture was then treated with 0.5M aqueous sodium hydroxide solution until basic and extracted with ethyl acetate. The combined extracts were washed with water (2×), dried (Na$_2$SO$_4$) and evaporated under reduced pressure, then the resulting residue purified by column chromatography on silica gel, eluting with a gradient of ethanol in dichloromethane (0 to 10% ethanol), to provide the title compound as a foam (145 mg). Rf 0.40 (SS 4). Found: C,66.41; H,8.20; N,7.16. C$_{22}$H$_{32}$N$_2$O$_2$S; 0.15 CH$_2$Cl$_2$ requires C,66.29; H,8.11; N, 6.97% δ(CDCl$_3$): 1.37(3H,t), 1.60–2.00(8H,m), 2.03–2.20 (2H,m), 2.30–2.48(2H,m), 2.62–2.98(5H,m), 3.05–3.16(1H, m), 3.18–3.44(6H,m), 5.30(0.30 H,s,CH$_2$Cl$_2$), 7.00(1H,d), 7.10(1H,s), 7.32(1H,d), 7.38(1H,s), 8.60(1H,br s).

EXAMPLE 19

3-[N-(2-Methoxyethyl)-2(R)-pyrrolidinylmethyl]-5-(2-phenylsulphonylethyl)-1H-indole Obtained as a gum, using Preparation 6 and 2methoxyethyl bromide. Rf 0.60 (SS 4). $[\alpha]_D^{25}$+23° (c=0.1, CH$_3$OH). Found: C,67.58; H,6.90; N,6.61. C$_{24}$H$_{30}$N$_2$O$_3$S requires C,67.57; H,7.09; N,6.57%. δ(CDCl$_3$): 1.50–1.85(4H,m), 2.25(1H,m), 2.50(1H,m), 2.55–2.80(2H,m), 3.08–3.30(6H, m), 3.35–3.45(4H,m), 3.50–3.60(2H,m), 6.90(1H,d), 7.02 (1H,br s), 7.24(1H,d), 7.30(1H,s), 7.56–7.68(3H,m), 7.90–8.00(3H,m).

EXAMPLE 20

3-[N-Cyclopropylmethyl-2(R)-pyrrolidinylmethyl)-5-(2-phenylsulphonylethyl)-1H-indole Obtained as a foam, using Preparation 6 and cyclopropylmethyl bromide. Rf 0.54 (SS 4). $[\alpha]_D^{25}$+5° (c=0.1, CH$_3$OH). Found: C,67.54; H,7.13; N,6.26. C$_{25}$H$_{30}$N$_2$O$_2$S; H$_2$O; 0.05 CH$_2$Cl$_2$ requires C,67.63; H,7.27; N,6.30%. δ(CDCl$_3$): 0.28(2H,m), 0.65(2H,m), 1.14(1H,m), 1.70–2.15 (4H,m), 2.30(1H,m), 2.62(1H,m), 2.80–3.12 (2H,m), 3.15–3.20(2H,m), 3.30–3.50(4H,m), 3.70(1H,m), 5.30 (0.10H,s,CH$_2$Cl$_2$), 6.94(1H,d), 7.20(1H,s), 7.28–7.34(2H, m), 7.60–7.75(3H,m), 8.00(2H,d), 8.20(1H,br s).

EXAMPLE 21

3-(N-Cyclopentyl-2(R)-pyrrolidinylmethyl)-5-(2-phenylsulphonylethyl)-1H-indole

Obtained as a foam, using preparation 6 and cyclopentyl iodide. Rf 0.52 (SS 4). $[\alpha]_D^{25}$+105° (c=0.1, CH$_3$OH). Found: C,66.95; H,7.25; N,6.27. C$_{26}$H$_{32}$N$_2$O$_2$S; 1.67 H$_2$O requires C,66.91; H,7.63 ; N,6.00%. δ(CDCl$_3$): 1.50–2.20 (12H,m), 2.80–3.05(3H,m) 3.10–3.20(3H,m), 3.30–3.60 (6H,m), 6.94(1H,d), 7.10(1H,s), 7.28(1H,d), 7.55–7.70(3H, m), 7.96(1H,d), 8.35(1H,br s).

EXAMPLE 22

3-[N-(3-Methyl-2-butenyl)-2(R)-pyrrolidinylmethyl]-5-(2-phenylsulphonylethyl)-1H-indole Obtained as a gum, using preparation 6 and 3-methyl-2-butenyl bromide. Rf 0.60 (SS 4). $[\alpha]_D^{25}$+6° (c=0.1, CH$_3$OH). Found: C,70.75; H,7.55; N,6.30. C$_{26}$H$_{32}$N$_2$O$_2$S; 0.10 CH$_2$Cl$_2$ requires C,70.43; H,7.29; N,6.29%. δ(CDCl$_3$): 1.50–1.85(10H,m), 2.22(1H,m), 2.50–2.70(2H,m), 2.92(1H, m), 3.10–3.22(4H,m), 3.40–3.50 (3H,m), 5.30(0.20H,s, CH$_2$Cl$_{12}$), 5.38(1H,m), 6.88(1H,d), 7.00(1H,s), 7.25(1H,d), 7.30(1H,s), 7.56–7.70(3H,m), 7.95–8.00(3H,m).

EXAMPLE 23

5-Bromo-3-(N-cyclopropylmethyl-2-(R)-pyrrolidinylmethyl)-1H-indole

Obtained as a foam, using preparation 7 and cyclopropylmethyl bromide. Rf 0.24 (SS 6). $[\alpha]_D^{25}$+72° (c=0.1, CH$_3$OH). Found: C,61.22; H,6.40; N,8.39. C$_{17}$H$_{26}$BrN$_2$ requires C, 61.26; H, 6.35; N,8.41%. δ(CDCl$_3$): 0.12–0.20 (2H,m), 0.50–0.58(2H,m), 0.92–1.08(1H,m), 1.50–1–92 (4H,m), 1.98–2.08(1H,m), 2.20–2.30(1H,m), 2.55–2.68(2H, m), 2.90–2.98(1H,m), 3.08–3.18 (1H,m), 3.38–3.50(1H,m), 7.04(1H,s), 7.20–7.28 (2H,m), 7.70(1H,s), 8.10(1H,br s).

EXAMPLE 24

5-Bromo-3-[N-(2-methoxyethyl)-2-(R)-pyrrolidinylmethyl]- 1H-indole

Obtained as an oil, using Preparation 7 and 2-methoxyethyl bromide. Rf 0.45 (SS 4). Found: C,57.25; H,6.41; N,8.14. C$_{16}$H$_{21}$Br N$_2$O requires C,56.98; H,6.28; N,8.31%. δ(CDCl$_3$): 1.46–1.90(4H,m), 2.18–2.31(1H,m), 2.42–2.52(1H,m), 2.55–2.75(2H,m), 3.05–3.30(3H,m), 3.40 (3H,s), 3.52–3.65(2H,m), 7.05(1H,s), 7.21–7.31(2H,m), 7.74(1H,s), 8.04(1H,br s).

EXAMPLE 25

5-Bromo-3-[N-(2-propyl)-2(R)-pyrrolidinylmethyl)-1H-indole

Obtained as a foam, using Preparation 7 and 2-iodopropane. Rf 0.24 (SS7). $[\alpha]_D^{25}$+66° (c=0.1, CH$_3$OH). Found: C,59.81; H,6.99; N,8.50. C$_{16}$H$_{21}$BrN$_2$ requires C,59.82; H,6.59; N,8.72%. δ(CDCl$_3$): 1.08(3H,d), 1.22(3H, d), 1.48–1.86(4H,m), 2.45–2.63(2H,m), 2.90–3.18(4H,m), 7.02(1H,s), 7.18–7.32(2H,s), 7.75(1H,s), 8.02(1H,br s).

EXAMPLE 26

5-(2-Ethylsulphonylethyl)-3-[N-(2-hydroxyethyl)-2(R) pyrrolidinylmethyl]-1H-indole To a stirred solution of 5-(2-ethylsulphonylethyl)-3-(2 (R)- pyrrolidinylmethyl)-1H-indole (Preparation 5; 350 mg, 1.1 mmol) in dry dimethylformamide (10 ml) at room temperature under nitrogen was added ethylene carbonate (160 mg, 1.8 mmol). The mixture was heated at 120° C. for 18 hours, allowed to cool, then partitioned between ethyl acetate and water. The organic phase was separated, washed with water (3×), dried (Na$_2$SO$_4$) and evaporated under reduced pressure to give a foam. Purification by column chromatography on silica gel, eluting initially with dichloromethane followed by a gradient of 0.880 aqueous ammonia:ethanol: dichloromethane (0:10:90 to 0.5:10:90), afforded the title compound as gum. Rf 0.35 (SS 4). Found: C,62.29; H,7.73; N,7.23. $C_{19}H_{28}N_2O_3S$; 0.05 $CH_2Cl_2$ requires C,62.04; H,7.68; N,7.60%. $\delta(CDCl_3)$: 1.35(3H,t), 1.50–1.90(5H,m), 2.30(1H,m), 2.50(1H,m), 2.70(1H,m), 2.80–3.35(10H,m), 3.60–3.75(2H,m), 5.30(0.10H,s, $CH_2Cl_2$), 7.00(1H,d), 7.05(1H,s), 7.25(1H,d), 7.40(1H,s), 8.25(1H,br s).

EXAMPLE 27

5-(2-Ethylsulphonylethyl)-3-{N-[2(S)-hydroxy-1-propyl]-2(R)-pyrrolidinylmethyl}-1H-indole To a stirred solution of 5-(2-ethylsulphonylethyl)-3-(2(R)- pyrrolidinylmethyl)-1H-indole hydrochloride (Preparation 5; 200 mg, 0.56 mmol) in methanol (2 ml) at room temperature under nitrogen was added triethylamine (0.09 ml). After 10 minutes, (S)-(−)-propylene oxide (0.05 ml, 0.71 mmol) and then water (12 ml) were added and the reaction mixture was warmed at 50° C. for 18 hours. The cool reaction mixture was evaporated under reduced pressure and the residue partitioned between ethyl acetate and water. The organic phase was separated, washed with water, dried ($Na_2SO_4$) and evaporated under reduced pressure to give an oil. Purification by column chromatography on silica gel, eluting with a gradient of ethanol in dichloromethane (0 to 10% ethanol), afforded the title compound as a gum (48 mg). Rf 0.50 (SS 4). $[\alpha]_D^{25}$+58° (c=0.1, $CH_3OH$). Found: C,57.44; H,7.58; N,6.39. $C_{20}H_{30}N_2O_3S$; 0.50 $H_2O$; 0.50 $CH_2Cl_2$ requires C,57.26; H,7.50; N,6.52%. $\delta(CDCl_3)$: 1.15 (3H,d), 1.38(3H,t), 1.50–1.90(4H,m), 2.20–2.38(2H,m), 2.60–2.75(2H,m), 2.85–2.95(3H,m), 3.10(1H,m), 3.20–3.38 (5H,m), 3.60– 3.90(2H,m), 5.30(1H,s,$CH_2Cl_2$), 7.02(1H,d), 7.05(1H,s), 7.32(1H,d), 7.40(1H,s), 8.10(1H,br s).

The following two compounds were obtained from Preparation 5, either as the free base or hydrochloride salt, using the appropriate epoxide alkylating agent and required amount of triethylamine as acid scavenger, by procedures similar to that described in Example 27.

EXAMPLE 28

5-(2-Ethylsulphonylethyl)-3-{N-[2(R)-hydroxy-1-propyl]-2(R)-pyrrolidinylmethyl}-1H-indole Obtained as a gum, using (R)-(+)-propylene oxide. Rf 0.50 (SS 4). $[\alpha]_D^{25}$+36° (c=0.1, $CH_3OH$). Found: C,59.92; H,7.80; N,6.97. $C_{20}H_{30}N_2O_3S$; 0.67 $H_2O$; 0.17 $CH_2Cl_2$ requires C,59.85; H,7.88; N,6.92%. $\delta(CDCl_3)$: 1.10(3H,d), 1.35(3H,t), 1.50–2.00(4H,m), 2.55(1H,m), 2.70–2.86(3H, m), 2.90(2H,q), 3.15–3.45(6H,m), 3.95(1H,m), 3.80–4.60 (1H,br s), 5.30(0.33H,s,$CH_2Cl_2$), 7.02(1H,d), 7.10(1H,s), 7.32(2H,d), 7.40(1H,s), 8.50(1H,br s).

EXAMPLE 29

5-(2-Ethylsulphonylethyl)-3-[N-(trans-2-hydroxycyclopenyl)-2(R)-2(R)-pyrrolidinylmethyl]-1H-indole Obtained as a gum, using cyclopentene oxide. Rf 0.30(SS 4). $[\alpha]_D^{25}$+11° (c=0.1, $CH_3OH$). Found: C,58.81; H,7.05; N,6.22. $C_{22}H_{32}N_2O_3S$; 0.50 $H_2O$; 0.50 $CH_2Cl_2$ requires C,59.25; H,7.51; N,6.14%. $\delta(CDCl_3)$- 1:1 mixture of two pairs of diastereoisomers: 1.34 and 1.36 (3H, 2×t), 1.50–2.20(10H,m), 2.70–3.04(5H,m), 3.10–3.65(8H,m), 4.22–4.42(1H,m), 5.30(1H,s,$CH_2Cl_2$), 6.98–7.05 and 7.18 (2H,m and s), 7.30 and 7.32(1H, 2×d), 7.45 and 7.55(1H, 2×s), 8.50 and 8.55(1H, 2×s).

EXAMPLE 30

5-(2-Ethylsulphonylethyl)-3-[N-(2-methylsulphonylethyl)-2(R)-pyrrolidinylmethyl]-1H-indole 5-(2-Ethylsulphonylethyl)-3-(2(R)-pyrrolidinylmethyl)-1H-indole hydrochloride (Preparation 5; 200 mg, 0.56 mmol) was dissolved in N,N-dimethylacetamide (4 ml) under nitrogen at room temperature, then methyl vinyl sulphone (0.06 ml, 0.69 mmol) and triethylamine (0.2 ml) were added. The resulting mixture was heated at 100° C. for 18 hours, allowed to cool, then partitioned between ethyl acetate and water. The organic phase was separated, washed with water, dried ($Na_2SO_4$) and evaporated under reduced pressure. The resulting crude material was purified by column chromatography on silica gel, eluting with a gradient of ethanol in dichloromethane (0 to 5% ethanol), to afford the title compound as a gum (130 mg). Rf 0.70 (SS 4). $[\alpha]_D^{25}$+43° (c=0.1, $CH_3OH$). Found: C,55.38; H,7.12; N,6.50. $C_{20}H_{30}N_2O_4S_2$; 0.10 $CH_2Cl_2$ requires C,55.48; H,7.00; N,6.44%. $\delta(CDCl_3)$: 1.38(3H,t), 1.50–1.90(5H,m), 2.22(1H, m), 2.60–2.80(3H,m), 2.90–3.35(12H,m), 3.48(1H,m), 5.30 (0.20H,s,$CH_2Cl_2$), 6.98–7.10(2H,m), 7.30(1H,d), 7.44(1H, s), 8.22(1H,br s).

The following twelve compounds were obtained from Preparation 5, 6 or 7, employed either as the free base or hydrochloride, using an appropriate "Michael acceptor" as alkylating agent, the required amount of triethylamine as acid scavenger, and a suitable solvent such as dimethylformamide, N,N-dimethylacetamide or 1,2-dimethoxyethane, by procedures similar to that described in Example 30.

EXAMPLE 31

5-(2-Ethylsulphonylethyl)-3-[N-{3-oxo-1-butyl)-2(R)-pyrrolidinylmethyl]-1H-indole Obtained as a gum, using Preparation 5 and methyl vinyl ketone. Rf 0.21 (SS 4). $[\alpha]_D^{25}$+19° (c=0.1, $CH_3OH$). Found: C,65.01; H,6.58; N,6.88. $C_{21}H_{30}N_2O_3S$ requires C, 64.58; H, 7.74; N, 7.17%. $\delta(CDCl_3)$: 1.35(3H,t), 1.50–1.80(4H,m), 2.18(3H,s), 2.45–2.76(6H,m), 2.95(2H,q), 3.10–3.38(7H, m.), 6.98–7.03(2H,m), 7.30(1H,d), 7.40(1H,s), 8.22(1H,br s).

EXAMPLE 32

3-[N-(2-t-Butoxycarbonylethyl)-2(R)-pyrrolidinylmethyl]-5-(2-ethylsulphonylethyl)-1H-indole Obtained as a gum, using Preparation 5 and t-butyl acrylate. Rf 0.60 (SS 4). $[\alpha]_D^{25}$+42° (c=0.1, $CH_3OH$). Found: C,61.97; H,7.67; N,5.93. $D_{24}H_{36}N_2O_4S$; 0.25 $CH_2Cl_2$ requires C,61.99; H,7.83; N,5.96%. $\delta(CDCl_3)$: 1.36 (3H,t), 1.40–1.80(13H,m), 2.20(1H,m), 2.45–2.65(5H,m), 2.92(2H,q), 3.10–3.35(7H,m), 5.30(0.50H,s,$CH_2Cl_2$), 6.96–7.04(2H,m), 7.30(1H,d), 7.42(1H,s), 8.35(1H,br s).

EXAMPLE 33

5-(2-Ethylsulphonylethyl]-3-{N-[2-(N,N-dimethylcarbamoyl)ethyl]-2(R)-pyrrolidinylmethyl}-1H-indole Obtained as a foam, using Preparation 5 and N,N-dimethylacrylamide. Rf 0.46 (SS 4). $[\alpha]_D^{25}$+39° (c=0.1, $CH_3OH$). Found: C,60.49; H,8.02; N,9.77. $C_{22}H_{33}N_3O_3S$; 0.33 H20; 0.125 $CH_2Cl_2$ requires C,60.92; H,7.84; N,9.63%. $\delta(CDCl_3)$: 1.42(3H,t), 1.58–1.90(4H,m), 2.35(1H,m), 2.62–2.75(4H,m), 2.84(1H,m), 2.90–3.05(9H,m), 3.15–3.48 (6H,m), 5.30(0.25H,s,$CH_2Cl_2$), 7.04–7.10(2H,m), 7.32(1H, d), 7.44(1H,s), 8.22(1H,br s).

EXAMPLE 34

3-[N-(2-Carbamoylethyl)-2(R)-pyrrolidinylmethyl]-5-(2-ethylsulphonylethyl-1H-indole Obtained as a foam, using preparation 5 and acrylamide. Rf 0.35 (SS 4). $[\alpha]_D^{25}$+55° (c=0.1, $CH_3OH$). Found: C,59.32; H,7.38; N,9.85. $C_{20}N_3O_3S$; 0.40 $H_2O$; 0.083 $CH_2Cl_2$; 0.25 $C_2H_5OH$ requires C,59.27; H,7.60; N,10.07%. δ($CDCl_3$): 1.27(0.75H, t,$C_2H_5OH$), 1.38(3H,t), 1.60–2.00(5H,m), 2.28(1H,m), 2.40 (1H,m), 2.55(2H,m), 2.70(1H,m), 2.84(1H,m), 2.95(2H,q), 3.25–3.38(6H,m), 3.65(0.5H.q,$C_2H_5OH$), 5.28(0.17H.s, $CH_2Cl_2$), 5.38(1H,br s), 7.04–7.06(2H,m), 7.35(1H,d), 7.45 (1H,s), 8.15(2H,br s).

EXAMPLE 35

5-2-Ethylsulphonylethyl)-3-N-2-sulphamoylethyl)-2(R)-pyrrolidinylmethyl]-1H-indole Obtained as a foam, using preparation 5 and vinyl sulphonamide. Rf 0.37 (SS 4). $[\alpha]_D^{25}$+48° (c=0.1, $CH_3OH$). Found: C,52.67; H,6.92; N,9.39. $C_{19}H_{29}N_3O_4S_2$; 0.10 $CH_2Cl_2$ requires C,52.60; H,6.75; N,9.64%. δ($CDCl_3$): 1.42 (3H,t), 1.55–1.95(5H,m), 2.30(1H,m), 2.70–2.87(2H,m), 2.95(2H,q), 3.14–3.40(7H,m), 3.62(2H,m), 5.10–5.70(2H,br s), 5.30(0.20H,s,$CH_2Cl_2$), 7.06(1H,d), 7.15(1H,s), 7.35(1H, d), 7.48(1H,s), 8.10(1H,br s).

EXAMPLE 36

5-2-Ethylsulphonylethyl)-3-N-2-2-pyridyl)ethyl]-2(R)-pyrrolidinylmethyl}-1H-indole Obtained as a foam, using preparation 5 and 2-vinylpyridine. Rf 0.57 (SS 4). $[\alpha]_D^{25}$+28° (c=0.1, $CH_3OH$). Found: C,65.97; H,7 .34; N,9.62. $C_{24}H_{31}N_3O_2S$; 0.67 $H_2O$ requires C,65.86; H,7.45; N,9.60%. δ($CDCl_3$): 1.42(3H,t), 1.65–2.00(4H,m), 2.55(1H,m), 2.75–3.05(5H, m), 3.14–3.35(7H,m), 3.42–3.54(2H,m), 7.05–7.10(2H,m), 7.15–7.28(2H,m), 7.35(1H,d), 7.46(1H,s), 7.65(1H,dd), 8.20(1H,br s), 8.56(1H,d).

EXAMPLES 37A AND 37B 5-(2-Ethylsulphonylethyl)-3-{N-[2(R)-phenylsulphinylethyl]-2(R)-pyrrolidinylmethyl}-1H-indole and
5-(2-Ethylsulphonylethyl)-3-{N-[2(S)-phenylsulphinylethyl]-2(R)-pyrrolidinylmethyl}-1H-indole The mixture of diastereoisomers obtained using Preparation 5 and phenyl vinyl sulphoxide was resolved by conventional column chromatography on silica gel to afford the title compounds as diastereoisomer 1 and diastereoisomer 2. However, which diastereoisomer corresponds with which title compound was not established.

Diastereoisomer 1

Obtained as a foam. Rf 0.52 (SS 4). $[\alpha]_D^{25}$+117° (c=0.1, $CH_3OH$). Found: C,63.74; H,6.57; N,5.72. $C_{25}H_{32}N_2O_3S_2$ requires C, 63.53; H, 6.82; N, 5.93%. δ($CDCl_3$): 1.42(3H,t), 1.60–1.95(5H,m), 2.30(1H,m), 2.65(1H,m), 2.85(1H,m), 2.94–3.10(4H,m), 3.20–3.40(6H,m), 3.60(1H,m), 7.05(1H, d), 7.20(1H,br s), 7.32(1H,d), 7.48(1H,s), 7.55–7.60(3H,m), 7.66–7.70(2H,m), 8.13(1H,br s).

Diastereoisomer 2

Obtained as a foam. Rf 0.48(SS 4). $[\alpha]_D^{25}$–37° (c=0.1, $CH_3OH$). Found: 62.39; H,6.29; N,5.34. $C_{25}H_{32}N_2O_3S_2$; 0.14 $CH_2Cl_2$ requires C,62.28; H,6.66; N,5.78. δ($CDCl_3$): 1.42(3H,t), 1.55–1.95(4H,m), 2.35(1H,m), 2.65(1H,m), 2.70 (1H,m), 2.94–3.20(6H,m), 3.25–3.40(6H,m), 5.30(0.28H,s, $CH_2Cl_2$), 7.05–7.10(2H,m), 7.35(1H,d), 7.40(1H,s), 7.56 (3H,m), 7.65–7.70(2H,m), 8.19(1H,br s).

EXAMPLE 38

3-[N-(3-Oxo-1-butyl)-2-(R)-pyrroldinylmethyl]-5-(2phenylsulphonylethyl)-1H-indole Obtained as a gum, using Preparation 6 and methyl vinyl ketone. Rf 0.60 (SS 4). $[\alpha]_D^{25}$+6° (c=0.1, $CH_3OH$). Found: C,67.64; H,6.86; N,6.20. $C_{25}H_{30 2}O_3S$; 0.10 $CH_2Cl_2$ requires C,67.43; H,6.81; N,6.27%. δ($CDCl_3$): 1.45–1.80(4H,m), 2.20(3H,s), 2.42–2.74(5H,m), 3.15–3.20(5H,m), 3.25–3.35 (1H,m), 3.40–3.42(2H,m), 5.30(0.20H,s,$CH_2Cl_2$), 6.92(1H, d), 7.00(1H,d), 7.22–7.38(2H,m), 7.55–7.70(3H,m), 7.96 (2H,d), 8.08(1H,br s).

EXAMPLE 39

3 -{N-[2-(N,N-Dimethylcarbamoyl)ethyl]-2(R)-pyrroldinylmethyl}-5-(2-phenylsulphonvlethyl)-1H-indole Obtained as a foam, using Preparation 6 and N,N-dimethylacrylamide. Rf 0.40 (SS 4). $[\alpha]_D^{25}$+33° (c=0.1, $CH_3OH$). Found:C,65.75; H,7.07; N,8.83. $C_{26}H_{33}N_3O_3$; 0.05 $CH_2Cl_2$; 0.25 $H_2O$ requires C,65.68; H,7.11; N,8.82%. δ($CDCl_3$): 1.48–1.96(4H,m), 2.20–2.35(1H,m), 2.50–2.80 (5H,m), 2.98(3H,s), 3.04(3H,s), 3.10–3.48(7H,m), 5.30 (0.10H,s,$CH_2Cl_2$), 6.92(1H,d), 7.02(1H,s), 7.22(1H,d), 7.30 (1H,s), 7.52–7.70(3H,m), 7.94–8.05(3H,m).

EXAMPLE 40

5-Bromo-3-{N-[2-(N,N-dimethylcarbamoyl)ethyl]-2(R)-pyrrolidinylmethyl}-1H-indole Obtained as a foam, using Preparation 7 and N,N-dimethylacrylamide. Rf 0.58 (SS 4). Found: C,55.53; H,6.18; N,10.66. $C_{18}H_{24}BrN_3O$; 0.20 $CH_2Cl_2$ requires C,55.30; H,6.22; N,10.63%. δ($CDCl_3$): 1.52–1.90(4H,m), 2.24–2.43(1H,m), 2.55–2.90(5H,m), 2.95(3H,s), 3.02(3H,s), 3.08–3.20(1H,s), 3.24–3.43(2H,m), 5.30(0.40H,s,$CH_2Cl_2$), 7.05(1H,s), 7.22–7.28(2H,m), 7.70(1H,s), 8.30(1H,br s).

EXAMPLE 41

5-Bromo-3-{N-[2-(N-methylcarbamoyl)ethyl]-2(R)-pyrrolidinylmethyl}- 1H-indole

Obtained as a foam, using Preparation 7 and N-methylacrylamide. Rf 0.54 (SS 4). $[\alpha]_D^{25}$+66° (c=0.1, $CH_3OH$). Found: C,55.53; H,5.96; N,11.42. $C_{17}H_{22}BrN_3O$ requires C,56.05; H,6.09; N,11.53%. δ($CDCl_3$): 1.53–1.90 (4H,m), 2.16–2.30(1H,m), 2.32–2.64(5H,m), 2.74(3H,d), 3.03–3.15(1H,m), 3.17–3.30(2H,m), 7.02(1H,d), 7.16–7.31 (2H,m), 7.69(1H,s), 8.08–8.30(2H,br m).

EXAMPLE 42

3- (N-Cyclopentylmethyl-2(R)-pyrrolidinylmethyl)-5-(2-ethylsulphonylethyl)-1H-indole Obtained as a foam by a procedure similar to that described in Example 18 (b), using Preparation 5 and cyclopentanecarboxylic acid. Rf 0.60 (SS 4). Found: C,67.74; H,8.55; N,6.81. $C_{23}H_{34}N_2O_2S$; 0.10 $CH_2Cl_2$ requires C,67.59; H,8.36; N,6.79. δ($CDCl_3$): 1.10–1.95 (14H,m), 2.08–2.22(1H,m), 2.30–2.42(2H,m), 2.70–2.98 (6H,m), 3.16–3.50(6H,m), 5.30(0.20H,s), 7.02(1H,d), 7.10 (1H,s), 7.32(1H,d), 7.42(1H,s), 8.35(1H,br s).

EXAMPLE 43

5-(2-Ethylsulphonylethyl)-3-{N-[2-(N-methylcarbamoyl) ethyl]-2(R)-pyrrolidinylmethyl}-1H-indole A solution of trifluoroacetic acid (0.25 ml) in dichloromethane (2 ml) was added to a stirred, ice-cold solution of 3-[N-(2-t-butoxycarbonylethyl)-2(R)pyrrolidinylmethyl]-5-(2-ethylsulphonylethyl)-1H-indole (Example 32; 250 mg). After 1 hour, the cooling bath was removed and stirring continued for 18 hours at room temperature. More trifluoroacetic acid (0.5 ml) was added, stirring continued for a further 8 hours, then evaporation under reduced pressure effected. Residual trifluoroacetic acid was removed from the crude product by azeotropic evaporation under reduced pressure using, sequentially, dichloromethane, ethyl acetate and dichloromethane, to provide a gum.

A sample of this crude carboxylic acid (100 mg) was stirred, together with 1-hydroxybenzotriazole (30 mg), N-methylmorpholine (0.1 ml) and 1-ethyl-3-dimethylaminopropylcarbodiimide hydrochloride (50 mg), in dichloromethane (5 ml) with ice-bath cooling. After 10 minutes methylamine hydrochloride (15 mg) was added, and stirring continued at 0° C. for 1 hour then at room temperature for 18 hours. The reaction mixture was diluted with dichloromethane, washed with water (2×), dried ($Na_2SO_4$) and evaporated under reduced pressure to afford the crude product as an oil. Purification was effected by column chromatography on silica gel, eluting with a solution of ethanol in dichloromethane (0 to 10% ethanol), to give the title compound (32 mg) as a gum. Rf 0.35 (SS4). $[\alpha]_D^{25}$+34° (c=0.1, $CH_3OH$). Found: C,60.58; H,7.39; N,9.36. $C_{21}H_{31}N_3O_3S$; 0.20 $CH_2Cl_2$ requires C,60.26; H,7.49; N,9.94%. $\delta(CDCl_3)$: 1.35(3H,t), 1.55–1.94(4H,m), 2.20–2.85(9H,m), 2.90(2H,q), 3.08–3.44(6H,m), 3.65(1H, m), 5.30(0.40 H,s,$CH_2Cl_2$), 7.00–7.08(2H,m), 7.32(1H,d), 7.40(1H,s), 8.15(1H,br s), 8.44(1H,m).

EXAMPLE 44

3-(N-Cyclopropylmethyl-2(R)-pyrrolidinomethyl)-5-(2-sulphamoylethenyl)-1H-indole Obtained as a foam by a procedure similar to that described in Preparation 3, using Example 23 and vinyl sulphonamide. Rf 0.19 (SS 6). $[\alpha]_D^{25}$+59° (c=0.1, $CH_3OH$). Found: C,61.47; H,7.11; N,11.18. $C_{19}H_{25}N_3O_2S$; 0.18 $CH_2Cl_2$ requires C,61.47; H,6.82; N,11.20%. $\delta(CDCl_3/CD_3OD)$: 0.06–0.15(2H,m), 0.42–0.54(2H,m), 0.80–0.90 (1H,m), 1.42–1.80(4H,m), 1.88–2.00(1H,m), 2.16–2.30 (1H,m), 2.42–2.65(2H,m), 2.84–2.94(1H,m), 3.04–3.10 (1H,m), 3.28–3.40(1H,m), 5.20(0.36H,s,$CH_2Cl_2$), 6.78 (1H, d), 6.98(1H,s), 7.18–7.32(2H,m), 7.48(1H,d), 7.55(1H,s).

PREPARATION 1

3-(N-Benzyloxycarbonyl-2(R)-pyrrolidinylcarbonyl)-5-bromo-1H-indole

Two solutions containing the reactants were prepared separately as follows. To a stirred solution of N-benzyloxycarbonyl-R-proline (1.0 g) in dry dichloromethane (2 ml) and dimethylformamide (1 drop) was added oxalyl chloride (0.5 ml), and the resulting solution was stirred at room temperature for 1.5 hours. The solution was evaporated under reduced pressure and the remaining solvent was removed under high vacuum to give the N-benzyloxycarbonyl-R-proline acid chloride. Concurrently, a solution of ethyl magnesium bromide (1.4 ml of a 3M solution in ether) was added dropwise over 5 minutes to a stirred solution of 5-bromoindole (0.75 g) in dry ether (18 ml). The mixture was stirred at room temperature for 10 minutes, heated under reflux for 2 hours, cooled to −30° C., and then a solution of the above N-benzyloxycarbonyl-R-proline acid chloride in dry ether (4 ml) added dropwise, after which stirring was continued for a further 1 hour. Ether (12.5 ml) and saturated aqueous sodium bicarbonate solution (6.5 ml) were then added and the temperature was allowed to rise to room temperature. Stirring was continued for a further 10 minutes and the mixture was filtered under reduced pressure. The solid was washed with ethyl acetate, then the combined filtrate and washings were washed with water and brine, then dried ($MgSO_4$). Evaporation under reduced pressure of the solvent gave an oil which was chromatographed on silica gel. Elution with ethyl acetate gave the title compound as a foam (0.82 g). $[\alpha]_D^{25}$+89° (c=0.1, $CH_3OH$). Found: C,58.85; H,4.51; N,6.38. $C_{21}H_{19}BrN_2O_3$ requires C,59.02; H,4.48; N,6.56%. LRMS: m/z (relative intensity) 428 ($M^+$ with $^{18}Br$,5), 426 ($M^+$ with $^{79}Br$, 5), 224 (19), 222 (21), 204 (62), 160 (68), 91 (100).

PREPARATION 2

3-(N-Benzyloxycarbonyl-2(R)-pyrrolidinylmethyl)-5-bromo-1H-indole 3-(N-Benzyloxycarbonyl-2(R)-pyrrolidinylcarbonyl)-5-bromo-1H-indole (Preparation 1; 0.67 g, 1.57 mmol) was dissolved in dry tetrahydrofuran (20 ml) and, at room temperature under nitrogen, lithium borohydride (2M solution in tetrahydrofuran; 1.2 ml, 2.4 mmol) was added. The reaction mixture was stirred at room temperature for 3 hours, heated under reflux for 16 hours, then allowed to cool to room temperature. 2N Hydrochloric acid (10 ml) was added dropwise and the reaction mixture then partitioned between ethyl acetate and water. The separated organic phase was washed with saturated aqueous sodium bicarbonate solution (2×) and brine (1×), dried ($Na_2SO_4$), and evaporated under reduced pressure to give a colourless oil. Purification by column chromatography on silica gel, eluting with dichloromethane, gave the title compound as an oil (0.32 g). Rf 0.20 (SS 1). Found: C,59.94; H,5.07; N,6.58. $C_{21}H_{21}BrN_2O_2$; 0.10 $CH_2Cl_2$ requires C,60.08; H,5.07; N,6.64%. $\delta(CDCl_3)$—mixture of rotamers: 1.63–1.90(4H, m), 2.60–2.82(1H,m), 3.10–3.28(1H,m), 3.30–3.54(2H,m), 4.18(1H,m), 5.15–5.25(2H,m), 5.30(0.2H,s,$CH_2Cl_2$), 6.90 and 6.95(1H, 2×s), 7.05–7.50(7H,m), 7.70 and 7.85(1H, 2×s), 8.25(1H,br s).

PREPARATION 3

3-(N-Benzyloxycarbonyl-2(R)-pyrrolidinylmethyl)-5-(2-ethylsulphonylethenyl)-1H-indole A stirred mixture of 3-(N-benzyloxycarbonyl-2(R)-pyrrolidinylmethyl)-5-bromo-1H-indole (Preparation 2; 0.43 g, 1.04 mmol), ethyl vinyl sulphone (0.17 g, 1.4 mmol), tri-o-tolylphosphine (91 mg), palladium(II) acetate (16 mg), triethylamine (0.31 ml) and acetonitrile (4 ml), under nitrogen, was heated under reflux for 18 hours, allowed to cool, then evaporated under reduced pressure. The residue was purified by column chromatography on silica gel, eluting with a dichloromethane to dichloromethane:ethanol (99:1) gradient, to afford the title compound as a foam (0.34 g). Rf 0.80 (SS 2). $[\alpha]_D^{25}$−50° (c=0.1, $CH_3OH$). Found: C,65.16; H,6.17; N,5.97. $C_{25}H_{28}N_2O_4S$; 0.125 $CH_2Cl_2$ requires C,65.15; H,6.15; N,6.05%. $\delta(CDCl_3)$—mixture of rotamers: 1.42(3H,t), 1.70–1.88(4H,m), 2.78(1H,m), 3.05–3.48(5H,m), 4.20(1H,m), 5.16–5.28(2H, br q), 5.30 (0.25H,s,$CH_2Cl_2$), 6.64–7.82(1H,m), 6.96 and 7.05(1H, 2×s), 7.30–7.45(7H,m), 7.55–7.80 and 8.00(2H, m and s), 8.32(1H,br s).

PREPARATION 4

3-(N-Benzyloxycarbonyl-2(R)-pyrrolidinylmethyl)-5-(2-phenylsulphonylethenyl)-1H-indole This was obtained by a procedure similar to that described in Preparation 3, but using phenyl vinyl sulphone instead of ethyl vinyl sulphone. The crude product was purified by column chromatography on silica gel, eluting with an ethyl acetate in hexane gradient (20 to 60% ethyl acetate), to afford the title compound as a foam. Rf 0.30 (SS 3). $[\alpha]_D^{25}$ −57° (c=0.1, $CH_3OH$). Found: C,69.62; H,5.62; N,5.58. $C_{29}H_{28}N_2O_4S$ requires C,69.58; H,5.64; N,5.59%. $\delta(CDCl_3)$—mixture of rotamers: 1.70–1.90(4H,m), 2.72 (1H,m), 3.16–3.50(3H,m), 4.18(1H,m), 5.18(2H,q), 6.70–7.00(2H,m), 7.28–7.60(10H,m), 7.68–8.00(4H,m), 8.25(1H,br s).

PREPARATION 5

5-(2-Ethylsulphonylethyl)-3-(2(R)-pyrrolidinylmethyl)-1H-indole

A solution of 3-(N-benzyloxycarbonyl-2(R)-pyrrolidinylmethyl)-5-(2-ethylsulphonylethenyl)-1H-indole (Preparation 3; 160 mg, 0.35 mmol) in ethanol (5 ml) was hydrogenated over 10% palladium on charcoal (150 mg) at 15 p.s.i. (1.04 bar) and room temperature for 18 hours, and then filtered. Evaporation of the filtrate under reduced pressure yielded a foam which was purified by column chromatography on silica gel, eluting with a gradient of 0.880 aqueous ammonia: methanol:dichloromethane (0:10:90 to 1:10:90), to provide the title compound as a foam (70 mg). Rf 0.30 (SS 4). $[\alpha]_D^{25}$ −11° (c=0.1, $CH_3OH$). Found: C,63.13; H,7.37; N,8.55. $C_{17}H_{24}N_2O_2S$; 0.05 $CH_2Cl_2$ requires C,63.07; H,7.48; N,8.63%. $\delta(CDCl_3)$: 1.35(3H,t), 1.65–1.90(5H,m), 2.70–3.10(6H,m), 3.25(4H,m), 3.35(1H, m), 5.25(0.10H,s, $CH_2Cl_2$), 6.98–7.04(2H,m), 7.22(1H,d), 7.45(1H,s), 8.12(1H,br s).

The hydrochloride salt was obtained by conducting the above hydrogenation in the presence of acetyl chloride (1.1 equiv.) and, after filtration of the reaction mixture and evaporation of the filtrate under reduced pressure, the crude salt was of sufficient purity for use in subsequent reactions.

PREPARATION 6

5-(2-Phenylsulphonylethyl)-3-(2(R)-pyrrolidinylmethyl) 1H-indole

The crude hydrochloride salt (2.2 g) of the title compound was obtained by a procedure similar to that described in Preparation 5, using 3-(N-benzyloxycarbonyl-2(R)-pyrrolidinylmethyl)-5-(2-phenylsulphonylethenyl)-1H-indole (Preparation 4; 2.81 g, 5.6 mmol), and was sufficiently pure for use in subsequent reactions.

A sample (300 mg) was partitioned between ethyl acetate and 2M aqueous sodium carbonate solution. The separated organic phase was washed with brine, dried ($Na_2SO_4$) and evaporated under reduced pressure to provide a white foam (270 mg). The crude free base was purified by column chromatography on silica gel, eluting initially with dichloromethane followed by a gradient of 0.880 aqueous ammonia:methanol: dichloromethane (0:10:90 to 1:10:90), to furnish the title compound as a foam. Rf 0.15 (SS 4). $[\alpha]_D^{25}$ −7° (c=0.1, $CH_3OH$). Found: C,66.66; H,6.27; N,7.40. $C_{21}H_{24}N_2O_2S$; 0.50 $H_2O$ requires C,66.81; H,6.68; N,7.42%. $\delta(CDCl_3)$: 1.42(1H,m), 1.65–1.95(3H,m), 2.60 (2H,br s, including 0.50 $H_2O$), 2.75–3.20(6H,m), 3.30–3.45 (3H,m), 6.84(1H,d), 7.02(1H,s), 7.25(1H,d), 7.30(1H,s), 7.52–7.70(3H,m), 7.92(2H,d), 8.30(1H,br s).

PREPARATION 7

5-Bromo-3-(2(R)-pyrrolidinylmethyl)-1H-indole

The title compound was prepared by either of the following methods.

(a)

A mixture of the title compound of Preparation 2 (10.0 g, 24.2 mmol) and a solution of hydrogen bromide in glacial acetic acid (36% w/w; 17 ml) was stirred at about 0° C. for 1 hour, then the solvent removed under reduced pressure and the residue azeotroped with toluene. The resulting oil was partitioned between dichloromethane and 2M aqueous sodium carbonate solution, then the organic phase separated, combined with a further dichloromethane extract of the aqueous phase, dried ($Na_2SO_4$) and evaporated under reduced pressure. Purification of the crude product by column chromatography on silica gel, eluting with a solvent gradient of 0.880 aqueous ammonia:methanol: dichloromethane (0:5:95 to 2:5:95), gave the title compound as an oil (2.01 g). Rf 0.10 (SS 4). $[\alpha]_D^{25}$ −9° (c=0.1, $CH_3OH$). Found: C,54.75; H,5.41; N,9.63. $C_{13}H_{15}BrN_2$; 0.20 $CH_2Cl_2$ requires C,54.84; H,5.37; N,9.67%. $\delta(CDCl_3)$: 1.35–1.50 (1H,m), 1.68–1.98(3H,m), 2.45(1H,br s), 2.72–2.92(3H,m), 2.96–3.08(1H,m), 3.28–3.43(1H,m), 5.28(0.40H,s,$CH_2Cl_2$), 7.06(1H,s), 7.18–7.26(2H,m), 7.72(1H,s), 8.52(1H,br s).

(b)

A solution of the title compound of Preparation 2 (5.0 g, 12.1 mmol) in dichloromethane was added dropwise to a stirred mixture of boron trifluoride etherate (17.15 g, 14.9 ml, 12.1 mmol) and ethanethiol (21.4 g, 25.5 ml, 344 mmol) at room temperature under nitrogen. After 68 hours the reaction mixture was poured into 10% aqueous sodium carbonate solution, then extraction with ethyl acetate (3×400 ml) effected. Evaporation under reduced pressure of the dried ($Na_2SO_4$), combined extracts, followed by column chromatography on silica gel of the crude product, eluting with 0.880 aqueous ammonia:methanol: dichloromethane (1:10:90), provided the title compound as a foam (2.10 g). Rf 0.10 (SS 4). $[\alpha]_D^{25}$ −12° (c=0.1, $CH_3OH$). Found: C,55.04; H,5.29; N,9.83. $C_{13}H_{15}BrN_2$; 0.06 $CH_2Cl_2$ requires C,55.10; N,5.35; N,9.83%. $\delta(CDCl_3)$: 1.38–1.50 (1H,m), 1.68–1.98(3H,m), 2.32(1H,br s), 2.76–2.90(3H,m), 3.00–3.10(1H,m), 3.32–3.41(1H,m), 5.30(0.12H,s,$CH_2Cl_2$), 7.06(1H,s), 7.22–7.30(2H,m), 7.75(1H,s), 8.37(1H,br s).

Biological Activity

The following Table illustrates the in vitro activities for a range of the Compounds of the invention on dog isolated saphenous vein strip. $EC_{50}$ represents the concentration of compound which causes 50% of the maximum contraction effected by it.

TABLE

| EXAMPLE | $EC_{50}(M)$ | RELATIVE POTENCY $EC_{50}$ (compound)/ $EC_{50}$ (5-HT) |
|---|---|---|
| 1 | 4.3 × 10⁻⁷ | 9.4 |
| 4 | 1.2 × 10⁻⁷ | 2.3 |
| 8 | 1.9 × 10⁻⁷ | 2.5 |
| 9 | 8.2 × 10⁻⁸ | 1.8 |
| 13 | 7.1 × 10⁻⁸ | 1.4 |
| 21 | 5.6 × 10⁻⁷ | 4.9 |
| 26 | 1.6 × 10⁻⁷ | 3.8 |
| 31 | 3.1 × 10⁻⁸ | 1.9 |
| 34 | 6.2 × 10⁻⁸ | 1.4 |
| 36 | 2.9 × 10⁻⁷ | 11.0 |

TABLE-continued

| EXAMPLE | $EC_{50}(M)$ | RELATIVE POTENCY $EC_{50}$ (compound)/ $EC_{50}$ (5-HT) |
|---|---|---|
| 37A (diastereoisomer 1) | $2.9 \times 10^{-7}$ | 4.6 |
| 38 | $4.4 \times 10^{-7}$ | 3.4 |
| 44 | $1.8 \times 10^{-7}$ | 2.7 |

Safety Profile

Several of the compounds of the invention have been tested in conscious dogs, for example Examples 8 and 13, and showed no signs of adverse acute toxicity at doses of up to 1 mg/Kg i.v.

We claim:

1. A compound of formula (I):

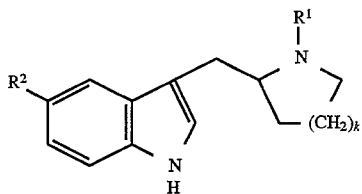

or a pharmaceutically acceptable salt thereof, wherein $R^1$ is $(R^3CO)C_1-C_3$ alkylene; $(R^4O_2C)C_1-C_3$ alkylene; $(R^5R^6NOC)C_1-C_3$ alkylene; $(R^5R^6NO_2S)C_1-C_3$ alkylene; $(R^3S(O)_m)C_1-C_3$ alkylene; $(R^7O)C_1-C_4$ alkylene; $(C_3-C_7$ cycloalkyl$)C_1-C_3$ alkylene; (aryl)$C_1-C_3$ alkylene; (heteroaryl)$C_1-C_3$ alkylene; $C_3-C_7$ cycloalkyl optionally substituted with HO; $C_3-C_6$ alkenyl optionally substituted with aryl; $C_5-C_7$ cycloalkenyl; or $C_3-C_6$ alkynyl;

$R^2$ is H; halo; $F_3C$; NC; $R^8R^9NOC$; $(R^8R^9NOC)C_1-C_3$ alkylene; $R^8R^9NO_2S$; $(R^8R^9NO_2S)C_1-C_3$ alkylene; $R^{10}S(O)_m$; $(R^{10}S(O)_m)C_1-C_6$ alkylene; $R^{12}CON(R^{11})$; $R^{12}CON(R^{11})]C_1-C_3$ alkylene; $R^{10}SO_2N(R^{11})$; $(R^{10}SO_2N(R^{11}))C_1-C_3$ alkylene; $R^{10}R^9NOCN$ $(R^{11})$; $(R^8R^9NOCN$ $(R^{11}))C_1-C_3$ alkylene; $R^{10}O_2CN$ $(R^{11})$; $(R^{10}O_2CN(R^{11}))C_1-C_3$ alkylene; or $R^{13}$ $(CH_2)_nCH=CH$;

$R^3$ is $C_1-C_6$ alkyl; $(C_3-C_7$ cycloalkyl$)C_1-C_3$ alkylene; (aryl)$C_1-C_3$ alkylene; $C_3-C_7$ cycloalkyl; or aryl;

$R^4$ is $C_1-C_6$ alkyl; $(C_3-C_7$ cycloalkyl$)C_1-C_3$ alkylene; (aryl)$C_1-C_3$ alkylene; or $C_3-C_7$ cycloalkyl;

$R^5$ and $R^6$ are each independently selected from H; $C_1-C_3$ alkyl; $(C_3-C_7$ cycloalkyl$)$ $C_1-C_3$ alkylene; (aryl) $C_1-C_3$ alkylene; and $C_3-C_7$ cycloalkyl;

$R^5$ and $R^6$ together with the nitrogen atom to which they are attached form a 4- to 7-membered heterocyclic ring which may optionally incorporate a further heteroatom linkage selected from O, $S(O)_m$, NH, $N(C_1-C_4$ alkyl), and $N(C_1-C_5$ alkanoyl);

$R^7$ is H; $C_1-C_6$ alkyl; $(C_3-C_7$ cycloalkyl$)C_1-C_3$ alkylene; (aryl)$C_1-C_3$ alkylene; $C_3-C_7$ cycloalkyl; or aryl;

$R^8$ and $R^9$ are each independently selected from H; $C_1-C_6$ alkyl; $(C_3-C_7$ cycloalkyl$)C_1-C_3$ alkylene; (aryl)$C_1-C_3$ alkylene; and $C_3-C_7$ cycloalkyl;

$R^8$ and $R^9$ together with the nitrogen atom to which they are attached form a 4- to 7-membered heterocyclic ring which may optionally incorporate a further heteroatom linkage selected from O, $S(O)_m$, NH, $N(C_1-C_4$ alkyl), and $N(C_1-C_5$ alkanoyl);

$R^{10}$ is $C_1-C_6$ alkyl; $(C_3-C_7$ cycloalkyl$)C_1-C_3$ alkylene; (aryl)$C_1-C_3$ alkylene; $C_3-C_7$ cycloalkyl; or aryl;

$R^{11}$ and $R^{12}$ are each independently selected from H; $C_1-C_6$ alkyl; $(C_3-C_7$ cycloalkyl$)C_1-C_3$ alkylene; (aryl) $C_1-C_3$ alkylene; $C_3-C_7$ cycloalkyl; and aryl;

$R^{13}$ is selected from $R^5R^9NOC$; $R^8R^9NO_2S$; $R^{10}S(O)_m$; $R^{12}CON(R^{11})$; $R^{10}SO_2N(R^{11})$; $R^8R^9NOCN(R^{11})$; and $R^{10}O_2CN(R^{11})$; wherein $R^8$, $R^9$, $R^{10}$, $R^{11}$ and $R^{12}$ are as defined above; and k, m and n are each independently selected from 0, 1 and 2, with the proviso that when m is 0, $R^{10}$ is not aryl.

2. A compound as claimed in claim 1 wherein $R^1$ is $(R^3CO)C_1-C_2$ alkylene; $(R^4O_2C)C_1-C_2$ alkylene; $(R^5R^6OC)C_1-C_2$ alkylene; $R^5R^6NO_2SCH_2CH_2$; $(R^3S(O)_m)C_1-C_2$ alkylene; $(R^7O)C_2-C_3$ alkylene; $(C_3-C_7$ cycloalkyl$)CH_2$; (phenyl)$C_1-C_2$ alkylene; (pyridyl)$C_1-C_2$ alkylene; $C_5-C_6$ cycloalkyl optionally substituted with HO; $C_3-C_5$ alkenyl optionally substituted with phenyl; or cyclohexenyl;

$R^2$ is $R^9NHOC$; $(R^9NHOC)C_1-C_2$ alkylene; $R^9NHO_2S$; $(R^9NHO_2S)C_1-C_2$ alkylene; $R^{10}SO_2$; $(R^{10}SO_2)C_1-C_2$ alkylene; $R^{12}CONH$; $(R^{12}CONH)C_1-C_2$ alkylene; $R^{10}SO_2NH$; $(R^{10}SO_2NH)C_1-C_2$ alkylene; or $R^{13}CH=CH$; $R^3$ is $C_1-C_6$ alkyl or aryl; $R^4$ is $C_1-C_6$ alkyl or (aryl)$C_1-C_3$ alkylene; $R^5$ and $R^6$ are each independently selected from H or $C_1-C_6$ alkyl; $R^7$ is H or $C_1-C_6$ alkyl; k is 1; and m is 1 or 2.

3. A compound as claimed in claim 2 wherein $R^1$ is $R^3COCH_2$; $R^3COCH_2CH_2$; $R^4O_2CCH_2$; $R^4O_2CCH_2CH_2$; $R^5R^6NOCCH_2$; $R^5R^6NOCCH_2CH_2$; $R^5R^6NOCCH(CH_3)$; $R^5R^6NO_2SCH_2CH_2$; $R^3S(O)_mCH_2CH_2$; $R^7OCH_2CH_2$; $R^7OCH(CH_3)CH_2$; $R^7OCH_2CH_2CH_2$; cyclopropylCH$_2$; cyclobutylCH$_2$; cyclopentylCH$_2$; benzyl; phenylCH$_2$CH$_2$; phenylCH(CH$_3$); pyridylCH$_2$; pyridylCH$_2$CH$_2$; cyclopentyl; hydroxycyclopentyl; allyl; pentenyl; cinnamyl; or cyclohexenyl; $R^2$ is $R^{10}SO_2CH_2CH_2$ or $R^9NHO_2SCH=CH$; $R^3$ is methyl or phenyl; $R^4$ is $(CH_3)_3C$ or benzyl; $R^5$ and $R^6$ are each independently selected from H or methyl; $R^7$ is H or methyl; $R^9$ is H or $C_1-C_6$ alkyl; and $R^{10}$ is $C_1-C_6$ alkyl or aryl.

4. A compound as claimed in claim 3 wherein $R^1$ is $CH_3COCH_2CH_2$; $(CH_3)_3CO_2CCH_2CH_2$; benzylO$_2$CCH$_2$; $H_2NOCCH_2CH_2$; $CH_3NHOCCH_2CH_2$; $(CH_3)_2NOCCH_2CH_2$; $H_2NO_2SCH_2CH_2$; phenylSOCH$_2$CH$_2$; HOCH$_2$CH$_2$; $CH_3OCH_2CH_2$; cyclopropylCH$_2$; cyclobutylCH$_2$; cyclopentylCH$_2$; phenylCH(CH$_3$); 2-pyridylCH$_2$; 4-pyridylCH$_2$; 2-pyridylCH$_2$CH$_2$; cyclopentyl; 2-hydrocyclopentyl; allyl; 3-methyl-2-butenyl; cinnamyl; or 3-cyclohexenyl; and $R^2$ is $CH_3CH_2SO_2CH_2CH_2$; phenylSO$_2$CH$_2$CH$_2$ or $H_2NO_2SCH=CH$.

5. A compound as claimed in claim 1 wherein the compound has the formula (IA):

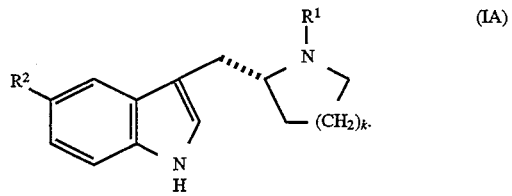

6. A pharmaceutical composition comprising a compound of formula (I), or a pharmaceutically acceptable salt thereof, as claimed in claim 1, together with a pharmaceutically acceptable diluent or carrier.

7. A method of treating a human being for migraine cluster headache, chronic paroxysmal hemicrania or headache associated with a vascular disorder, or depression, anxiety, an eating disorder, obesity or drug abuse, which comprises treating said human being with an effective amount of a compound of formula (I), or a pharmaceutically acceptable salt thereof, or a pharmaceutical composition as claimed in claim 1.

8. A method of treating a human being for a medical condition for which a selective agonist of $5\text{-HT}_1$-like receptors is indicated, which comprises treating said human being with an effective amount of a compound of formula (I), or a pharmaceutically acceptable salt thereof, or a pharmaceutical composition as claimed in claim 1.

* * * * *